(12) United States Patent
Pham et al.

(10) Patent No.: US 10,335,308 B2
(45) Date of Patent: Jul. 2, 2019

(54) FLEXIBLE BARRIER FILMS CONTAINING CYCLIC OLEFINS

(71) Applicant: Avery Dennison Corporation, Glendale, CA (US)

(72) Inventors: Hoang T. Pham, Painesville, OH (US); Farid F. Ghiam, Beachwood, OH (US); Thomas Laney, Spencerport, NY (US)

(73) Assignee: Avery Dennison Corporation, Glendale, CA (US)

(*) Notice: Subject to any disclaimer, the term of this patent is extended or adjusted under 35 U.S.C. 154(b) by 1097 days.

(21) Appl. No.: 14/367,275

(22) PCT Filed: Dec. 13, 2012

(86) PCT No.: PCT/US2012/069413
§ 371 (c)(1),
(2) Date: Jun. 20, 2014

(87) PCT Pub. No.: WO2013/096078
PCT Pub. Date: Jun. 27, 2013

(65) Prior Publication Data
US 2015/0018788 A1    Jan. 15, 2015

Related U.S. Application Data

(60) Provisional application No. 61/579,170, filed on Dec. 22, 2011, provisional application No. 61/675,981, filed on Jul. 26, 2012.

(51) Int. Cl.
*A61F 5/441*    (2006.01)
*C08L 57/00*    (2006.01)
(Continued)

(52) U.S. Cl.
CPC ............ *A61F 5/441* (2013.01); *B32B 7/02* (2013.01); *B32B 27/08* (2013.01); *B32B 27/306* (2013.01);
(Continued)

(58) Field of Classification Search
CPC ...................................... A61F 5/441
See application file for complete search history.

(56) References Cited

U.S. PATENT DOCUMENTS 2,847,845 A    6/1956    Frank et al.
3,510,464 A    5/1970    Sato
(Continued)

FOREIGN PATENT DOCUMENTS

CN    101687584    3/2010
CN    102476493    5/2012
(Continued)

OTHER PUBLICATIONS

International Search Report and Written Opinion issued in corresponding IA No. PCT/US2012/069413, dated Mar. 5, 2013.
(Continued)

*Primary Examiner* — Tatyana Zalukaeva
*Assistant Examiner* — Guy K Townsend
(74) *Attorney, Agent, or Firm* — Avery Dennison Corporation

(57) ABSTRACT

Various polymeric barrier compositions are described which when formed into films, are useful in reducing transmission of odors. The films can be incorporated into a wide range of products such as multilayer barrier films used in medical applications and particularly in ostomy appliances. In certain versions, the films include blends of amorphous cyclic olefin copolymers and semi-crystalline cyclic olefin copolymers.

51 Claims, 3 Drawing Sheets

(51) Int. Cl.
  *B32B 7/02*   (2019.01)
  *B32B 27/08*  (2006.01)
  *B32B 27/30*  (2006.01)
  *B32B 27/32*  (2006.01)

(52) U.S. Cl.
  CPC ............ *B32B 27/32* (2013.01); *B32B 27/325* (2013.01); *C08L 57/00* (2013.01); *B32B 2250/24* (2013.01); *B32B 2250/246* (2013.01); *B32B 2270/00* (2013.01); *B32B 2274/00* (2013.01); *B32B 2307/7244* (2013.01); *B32B 2439/46* (2013.01); *B32B 2439/80* (2013.01); *Y10T 428/3192* (2015.04); *Y10T 428/31913* (2015.04); *Y10T 428/31938* (2015.04)

(56) References Cited

U.S. PATENT DOCUMENTS

| | | | |
|---|---|---|---|
| 3,560,461 A | 2/1971 | Mukumoto et al. | |
| 3,585,177 A | 6/1971 | Gardner et al. | |
| 3,595,740 A | 7/1971 | Gerow | |
| 3,985,826 A | 10/1976 | Futamura | |
| 4,034,079 A | 7/1977 | Schoonman | |
| 4,237,114 A | 12/1980 | Cardarelli | |
| 4,254,169 A | 3/1981 | Schroeder | |
| 4,687,711 A | 8/1987 | Vietto et al. | |
| 4,881,649 A | 11/1989 | Hsu et al. | |
| 4,983,171 A | 1/1991 | Schirmer | |
| 5,093,164 A | 3/1992 | Bauer et al. | |
| 5,218,049 A | 6/1993 | Yamamoto et al. | |
| 5,300,352 A | 4/1994 | Honma | |
| 5,371,158 A | 12/1994 | Rohrmann et al. | |
| 5,407,713 A | 4/1995 | Wilfong et al. | |
| 5,455,091 A | 10/1995 | Oreglia et al. | |
| 5,470,624 A | 11/1995 | Oreglia et al. | |
| 5,496,295 A | 3/1996 | Wilfong et al. | |
| 5,532,030 A | 7/1996 | Hirose et al. | |
| 5,567,488 A | 10/1996 | Allen et al. | |
| 5,567,489 A | 10/1996 | Allen et al. | |
| 5,567,495 A | 10/1996 | Modak et al. | |
| 5,643,375 A | 7/1997 | Wilfong et al. | |
| 5,658,625 A | 8/1997 | Bradfute et al. | |
| 5,708,083 A | 1/1998 | Furushima et al. | |
| 5,730,919 A | 3/1998 | Wilfong et al. | |
| 5,766,699 A | 6/1998 | Ohtsuki et al. | |
| 5,912,070 A | 6/1999 | Miharu et al. | |
| 5,929,133 A | 7/1999 | Watanabe et al. | |
| 5,983,604 A | 11/1999 | Wilfong et al. | |
| 5,993,949 A | 11/1999 | Rosenbaum et al. | |
| 6,042,906 A | 3/2000 | Itoh | |
| 6,068,936 A | 5/2000 | Peiffer et al. | |
| 6,143,383 A | 11/2000 | Giori | |
| 6,258,423 B1 | 7/2001 | Giori | |
| 6,294,609 B1 | 9/2001 | Bertin et al. | |
| 6,312,772 B1 | 11/2001 | Kuder et al. | |
| 6,329,047 B1 | 12/2001 | Beer et al. | |
| 6,455,161 B1 | 9/2002 | Regnier et al. | |
| 6,489,016 B2 | 12/2002 | Kishine | |
| 6,579,584 B1 | 6/2003 | Compton | |
| 6,620,474 B1 | 9/2003 | Regnier et al. | |
| 6,812,292 B2 | 11/2004 | Matsukawa et al. | |
| 6,852,100 B1 | 2/2005 | Gent et al. | |
| 6,884,480 B2 | 4/2005 | Bradfute et al. | |
| 6,921,563 B2 | 7/2005 | Goerlitz et al. | |
| 6,984,442 B2 | 1/2006 | Brebion et al. | |
| 7,147,845 B2 | 12/2006 | Capelli | |
| 7,270,860 B2 | 9/2007 | Giori | |
| 7,271,209 B2* | 9/2007 | Li ............................ C08K 5/01 524/284 |
| 7,288,316 B2 | 10/2007 | Jester | |
| 7,524,910 B2* | 4/2009 | Jiang ..................... C08F 10/00 526/348 |
| 7,531,594 B2* | 5/2009 | Lin .......................... C08K 5/01 524/474 |
| 7,605,217 B2 | 10/2009 | Datta et al. | |
| 7,629,416 B2 | 12/2009 | Li et al. | |
| 7,645,505 B2 | 1/2010 | Bekele et al. | |
| 7,863,264 B2 | 1/2011 | Nielsen et al. | |
| 7,998,579 B2* | 8/2011 | Lin ..................... C08K 5/0016 428/364 |
| 8,022,144 B2 | 9/2011 | Chang et al. | |
| 8,092,877 B2 | 1/2012 | Jester et al. | |
| 2,459,377 A1 | 6/2012 | Bekele | |
| 8,192,813 B2* | 6/2012 | Runyan .................. B29C 71/04 428/35.7 |
| 8,206,818 B2 | 6/2012 | Bekele et al. | |
| 8,299,193 B2 | 10/2012 | Suzuki et al. | |
| 8,377,529 B2* | 2/2013 | Bekele ..................... B32B 7/12 428/35.2 |
| 8,435,642 B2 | 5/2013 | Bekele | |
| 8,562,885 B2* | 10/2013 | Dooley ............... B29C 47/0023 264/171.27 |
| 8,663,799 B2* | 3/2014 | Lin .......................... D01F 1/10 428/364 |
| 8,900,719 B2* | 12/2014 | Pham ..................... B32B 25/08 428/518 |
| 9,283,735 B2* | 3/2016 | Pham ..................... B32B 27/08 |
| 9,481,143 B2* | 11/2016 | Dooley ............... B29C 47/0023 |
| 2003/0118758 A1* | 6/2003 | Chen ........................ B32B 1/02 428/35.2 |
| 2003/0124289 A1 | 7/2003 | Jun et al. | |
| 2003/0186955 A1 | 10/2003 | Nielsen et al. | |
| 2003/0223657 A1 | 12/2003 | Belias et al. | |
| 2004/0186214 A1* | 9/2004 | Li ............................ C08K 5/01 524/474 |
| 2004/0247915 A1 | 12/2004 | Wuest et al. | |
| 2004/0260001 A1* | 12/2004 | Lin .......................... C08K 5/01 524/474 |
| 2005/0244665 A1* | 11/2005 | Rivett ................... A23L 3/3436 428/500 |
| 2005/0249791 A1 | 11/2005 | Hobbs | |
| 2006/0008643 A1* | 1/2006 | Lin ..................... C08K 5/0016 428/364 |
| 2006/0062946 A1 | 3/2006 | Beer et al. | |
| 2006/0210739 A1 | 9/2006 | Loffler et al. | |
| 2006/0211804 A1* | 9/2006 | Kim ........................ B32B 7/12 524/445 |
| 2006/0247331 A1 | 11/2006 | Lundmark et al. | |
| 2006/0251876 A1 | 11/2006 | Goerlitz et al. | |
| 2007/0021566 A1* | 1/2007 | Tse ....................... C09D 123/10 525/240 |
| 2007/0040350 A1 | 2/2007 | Bertrand et al. | |
| 2007/0055015 A1 | 3/2007 | Flood et al. | |
| 2007/0110853 A1* | 5/2007 | Bekele ................... B32B 27/32 426/106 |
| 2007/0202337 A1 | 8/2007 | Lischefski et al. | |
| 2007/0237916 A1 | 10/2007 | Rasmussen et al. | |
| 2008/0152837 A1 | 6/2008 | Chien et al. | |
| 2008/0220036 A1 | 9/2008 | Miltz et al. | |
| 2008/0281045 A1 | 11/2008 | Zhang | |
| 2008/0292225 A1* | 11/2008 | Dayrit .................... B32B 27/08 383/207 |
| 2009/0036862 A1 | 2/2009 | Grimm | |
| 2009/0163632 A1 | 6/2009 | Hatke et al. | |
| 2009/0208685 A1 | 8/2009 | Rivers et al. | |
| 2009/0216207 A1 | 8/2009 | Nielsen | |
| 2010/0012190 A1 | 5/2010 | Rasmussen et al. | |
| 2010/0119746 A1* | 5/2010 | Igarashi ................. B32B 27/32 428/35.7 |
| 2010/0121290 A1 | 5/2010 | Rasmussen et al. | |
| 2010/0215879 A1* | 8/2010 | Dooley ............... B29C 47/0023 428/35.7 |
| 2010/0236090 A1 | 9/2010 | Grimm | |
| 2010/0272831 A1 | 10/2010 | Cabedo et al. | |
| 2011/0027428 A1* | 2/2011 | Bekele ..................... B32B 7/12 426/127 |
| 2011/0213048 A1 | 9/2011 | Yoo et al. | |
| 2011/0256373 A1 | 10/2011 | Tatarka et al. | |
| 2012/0021151 A1 | 1/2012 | Tatarka et al. | |
| 2012/0258326 A1* | 10/2012 | Pham ..................... B32B 25/08 428/518 |

(56) References Cited

U.S. PATENT DOCUMENTS

| | | | | |
|---|---|---|---|---|
| 2013/0025764 A1* | 1/2013 | Henderson | ............ | A01N 25/10 |
| | | | | 156/60 |
| 2013/0156983 A1* | 6/2013 | Pham | ............ | B32B 27/08 |
| | | | | 428/36.7 |
| 2014/0044906 A1* | 2/2014 | Dooley | ............ | B29C 47/0023 |
| | | | | 428/36.91 |
| 2014/0194024 A1* | 7/2014 | Pham | ............ | B32B 5/022 |
| | | | | 442/396 |
| 2015/0018788 A1* | 1/2015 | Pham | ............ | B32B 7/02 |
| | | | | 604/333 |
| 2015/0225151 A1* | 8/2015 | Osborn | ............ | B32B 15/085 |
| | | | | 604/307 |
| 2015/0282978 A1* | 10/2015 | Henderson | ............ | B32B 25/08 |
| | | | | 604/333 |

FOREIGN PATENT DOCUMENTS

| | | |
|---|---|---|
| DE | 10101902 | 7/2002 |
| EP | 0437152 | 7/1991 |
| EP | 0518542 | 9/1996 |
| EP | 0485893 | 4/1998 |
| EP | 0617665 | 3/1999 |
| EP | 0911150 | 5/1999 |
| EP | 0719209 | 1/2000 |
| EP | 0719210 | 1/2000 |
| EP | 0974453 | 4/2000 |
| EP | 0433060 | 5/2000 |
| EP | 0765909 | 3/2001 |
| EP | 0800914 | 7/2002 |
| EP | 0824067 | 10/2003 |
| EP | 1391294 | 2/2004 |
| EP | 1398149 | 3/2004 |
| EP | 0765219 | 4/2004 |
| EP | 0958916 | 8/2004 |
| EP | 1322168 | 11/2004 |
| EP | 1081058 | 12/2004 |
| EP | 1487634 | 12/2004 |
| EP | 0970672 | 3/2005 |
| EP | 1364777 | 8/2005 |
| EP | 1682350 | 7/2006 |
| EP | 1687355 | 8/2006 |
| EP | 1622765 | 10/2006 |
| EP | 1422057 | 1/2007 |
| EP | 1525092 | 5/2007 |
| EP | 1825997 | 8/2007 |
| EP | 1196482 | 1/2008 |
| EP | 1944331 | 7/2008 |
| EP | 1983948 | 10/2008 |
| EP | 1985585 | 10/2008 |
| EP | 2077944 | 7/2009 |
| EP | 2176137 | 4/2010 |
| EP | 2001671 | 5/2010 |
| EP | 1531987 | 12/2011 |
| EP | 2164898 | 8/2012 |
| EP | 2050771 | 4/2013 |
| EP | 1958973 | 6/2014 |
| JP | 198089336 | 7/1980 |
| JP | 60-1246 | 7/1985 |
| JP | 1989186804 | 7/1989 |
| JP | 04148640 | 5/1992 |
| JP | 1992359028 | 12/1992 |
| JP | 5051468 | 3/1993 |
| JP | 5132590 | 5/1993 |
| JP | 05140369 | 6/1993 |
| JP | 8333466 | 12/1996 |
| JP | 10129736 | 5/1998 |
| JP | 10272742 | 10/1998 |
| JP | 1989306473 | 12/1998 |
| JP | 11309822 | 11/1999 |
| JP | 2000128112 | 5/2000 |
| JP | 2000211066 | 8/2000 |
| JP | 2001038862 | 2/2001 |
| JP | 2001072717 | 3/2001 |
| JP | 2001293816 | 10/2001 |
| JP | 2001301093 | 10/2001 |
| JP | 2003011303 | 1/2003 |
| JP | 2004262226 | 9/2004 |
| JP | 2008036863 | 2/2008 |
| JP | 2008068877 | 3/2008 |
| JP | 2008174576 | 7/2008 |
| JP | 2008195890 | 8/2008 |
| JP | 2009003439 | 1/2009 |
| JP | 2009051922 | 3/2009 |
| JP | 2009175721 | 8/2009 |
| JP | 2009227810 | 10/2009 |
| JP | 2011043628 | 3/2011 |
| JP | 2011111573 | 6/2011 |
| KR | 20080051547 | 6/2008 |
| WO | WO9216358 | 10/1992 |
| WO | WO1996029361 | 9/1996 |
| WO | WO1999054133 | 10/1999 |
| WO | WO2003018312 | 3/2003 |
| WO | WO2003040442 | 5/2003 |
| WO | WO2003055678 | 7/2003 |
| WO | WO2003055681 | 7/2003 |
| WO | WO2005042241 | 12/2005 |
| WO | WO2006009360 | 1/2006 |
| WO | WO2008128896 | 10/2008 |
| WO | WO2008139593 | 11/2008 |
| WO | WO2009096921 | 8/2009 |
| WO | WO2009105205 | 8/2009 |
| WO | 2011/129982 | 10/2011 |
| WO | WO2011129982 | 10/2011 |
| WO | 2011/162414 | 12/2011 |

OTHER PUBLICATIONS

European Search Report issued in corresponding EP Application No. 15000737.5 dated May 28, 2015.

Brzeziński, et al., Bacteriostatic textile-polymeric coat materials modified with nanoparticles, Polimery, 52 (2007) 362-366.

Choi, et al., "The inhibitory effects of silver nanoparticles, silver ions, and silver chloride colloids on microbia growth", Water Research 42 (2008) 3066-304; Mar. 4, 2008.

E. L. Zakharova et al: "Use of Ethylene—Vinyl Acetate Copolymers for Creating Long-Acting Therapeutic Systems With Controlled Release of Agents (Review)",Pharmaceutical Chemistry Journal, val. 27, No. 11, (Nov. 1, 1993 ), pp. 739-747.

International Search Report and the Written Opinion of the International Searching Authority, or the Declaration, dated May 16, 2013.

International Search Report and the Written Opinion of the International Searching Authority, or the Declaration, dated Oct. 31, 2012.

International Search Report and the Written Opinion of the International Searching Authority, or the Declaration, dated Sep. 5, 2012.

International Search Report and Written Opinion of the International Searching Authority, dated Apr. 19, 2012.

International Search Report, dated Oct. 10, 2012.

Invitation to pay additional fees, dated Apr. 16, 2012.

Li, et al., "Antimicrobial nanomaterials for water disinfection and microbial control: Potential applications and implications", Water Research 42 (2008) 4591-4602.

Li, et al., "In vitro drug release study of methacrylate polymer blend system: effect of polymer blend composition, drug loading and solubilizing surfactants on drug release", Journal of Materials Science: Materials in Medicine, 2, (2010) vol. 21, 583-588.

M. B. Fedorov et al: "Antimicrobial activity of core-sheath surgical sutures modified with poly-3-hydroxybutyrate", Applied Biochemistry and Microbiology, val. 43, No. 6, (Nov. 1, 2007 ), pp. 611-615.

Mistry, Development of LDPE-based Antimicrobial Films for Food Packaging, Jul. 2006.

Ruggeri, et al., "Synthesis, characterization, and in vitro activity of antibiotic releasing polyurethanes to prevent bacterial resistance", Journal of Biomedical Materials Research Part A, 2, (2007), vol. 81A, 287-298.

Tallury, et al., "Effects of solubilizing surfactants and loading of antiviral antimicrobial, and antifungal drugs on their release rates from ethylene vinyl acetate copolymer", Dental Materials, 23, (20070 977-982).

(56) References Cited

OTHER PUBLICATIONS

Tallury, et al., "Poly(ethylenecovinyl acetate) copolymer matrix for delivery of chlorhexidine and acyclovir drugs for use in the oral environment: Effect of drug combination, copolymer composition and coating on the drug release rate", Dental Materials, 23 (2007) vol. 23, 404-409.

Uttarwar, et al., "Fabrication of Porous, Drug-Releasing, Biodegradable, Polymer Scaffolds for Sustained Drug Release", Journal of Biomedical Materials Research Part B Applied Biomaterials, 1, (2008), vol. 87B, 121-131.

Written Opinion of the International Searching Authority, dated Oct. 10, 2012.

Zakharova, et al, "Use of Ethylene-Vinyl Acetate Copolymers for Creating Long-Acting Therapeutic Systems with Controlled Release of Agents (Review)", Pharmeceutical Chemistry Journal, 11, (1993) vol. 27.

\* cited by examiner

FLEXIBLE BARRIER FILMS CONTAINING CYCLIC OLEFINS

CROSS REFERENCES TO RELATED APPLICATIONS

The present application is a 371 of International Application No. PCT/US2012/069413, which was published in English on Jun. 27, 2013, which claims priority to U.S. Provisional Patent Application No. 61/579,170 filed Dec. 22, 2011 and U.S. Provisional Patent Application No. 61/675,981 filed Jul. 26, 2012, all of which are incorporated herein by reference in their entireties.

FIELD

The present subject matter relates to polymeric barrier films for reducing transmission of odors. The subject matter also relates to articles comprising such films. The subject matter additionally relates to methods for reducing transmission of odors by use of the polymeric barrier films. The films, articles, and methods associated therewith are useful in various fields such as medical and health care applications, and find particular application in ostomy appliances and devices.

BACKGROUND

Barrier films in medical applications and particularly as used in ostomy applications, typically contain halogens. An example of a material used in such applications is polyvinylidene chloride (PVDC). Although use of that material is satisfactory in many regards, films containing halogens such as chloride and bromide are difficult and costly to recycle. In fact, with increasing environmental awareness, many regulations prohibit the disposal of halogens, thereby further increasing the inconvenience and/or cost of handling used medical products containing halogens.

Many currently known barrier films and particularly those used in certain medical applications, employ one or more layers that contain amorphous cyclic olefin copolymers (COCs). However, incorporating COCs into a thin multilayer film presents a formidable technical challenge, particularly if other characteristics of the film are to be maintained such as flexibility, strength, and ability to be joined with other material(s) to form articles or goods. Accordingly, a need remains for a barrier film that provides comparable or superior odor blocking properties as currently known barrier films, without compromising flexibility, strength, and other characteristics.

Moreover, cyclic olefin copolymers or similar compounds containing norbornene typically exhibit relatively high levels of rigidity such that when polymeric films containing such are subjected to deformation or flexure, the films emit noise from "crinkling" or "rustling" of the film. When such films are used in certain medical applications such as in as ostomy bag, emission of such noise is undesirable. In view of the required barrier properties of the films for such applications, it is not always possible to reduce the concentration or amount of cyclic olefin in the film. Thus, a need exists for one or more strategies by which noise produced by films containing cyclic olefins or norbornene can be reduced.

SUMMARY

The difficulties and drawbacks associated with previously known films and articles are addressed in the barrier films, articles using such films, and related methods described herein.

In one aspect, a barrier film is provided which comprises a blend of cyclic olefin copolymers (COC) wherein the blend includes a semi-crystalline cyclic olefin copolymer (COC), and the total norbornene concentration in the barrier film is from about 12 mole % to about 60 mole %, more preferably from about 15 mole % to about 55 mole %, and most preferably from about 18 mole % to about 50 mole %.

In another aspect, a barrier film is provided which comprises a semi-crystalline cyclic olefin copolymer (COC) having a melting temperature (Tm) of from about 70° C. to about 120° C., a glass transition temperature (Tg) of from about −20° C. to about 20° C., and a norbornene content of from about 5% to about 25% by mole.

In still another aspect, a multilayer barrier film is provided comprising at least one layer including a blend of cyclic olefin copolymers (COC) wherein the blend includes a semi-crystalline cyclic olefin copolymer (COC), and the total norbornene concentration in the layer is from about 12 mole % to about 60 mole %, more preferably from about 15 mole % to about 55 mole %, and most preferably from about 18 mole % to about 50 mole %.

In still a further aspect, a multilayer barrier film is provided which comprises at least one layer including semi-crystalline cyclic olefin copolymer (COC) having a melting temperature (Tm) of from about 70° C. to about 120° C., a glass transition temperature (Tg) of from about −20° C. to about 20° C., and a norbornene content of from about 5% to about 25% by mole.

Additionally, various articles such as ostomy pouches formed from the noted barrier layers and multilayer barriers are provided.

Also provided are methods for reducing transmission of odorous species. The methods comprise providing a semi-crystalline cyclic olefin copolymer (COC), and forming a film including the semi-crystalline COC. The methods also comprise positioning the film between a source of odorous species and a user.

Additional methods are provided for reducing transmission of odorous species. The methods comprise providing at least one layer including a blend of cyclic olefin copolymers (COC) wherein the blend includes a semi-crystalline cyclic olefin copolymer (COC), and the total norbornene concentration in the layer is from about 12 mole % to about 60 mole %, more preferably from about 15 mole % to about 55 mole %, and most preferably from about 18 mole % to about 50 mole %. The methods also comprise forming a film including the at least one layer including a blend of cyclic olefin copolymers (COC). The methods also comprise positioning the film between a source of odorous species and a user.

In still another aspect, the present subject matter provides a multilayer barrier film defining a central plane. The barrier film comprises a plurality of layers each including at least one COC containing norbornene. The concentration of norbornene in each layer of the plurality of layers decreases with increased distance from the central plane.

In another aspect, the present subject matter provides a multilayer barrier film defining a central layer through which extends a central plane. The central layer defines a first face and an oppositely directed second face. The barrier film comprises a first layer including at least one COC. The first layer is disposed immediately adjacent to the first face of the central layer. The barrier film also comprises a second layer including at least one COC. The second layer is disposed immediately adjacent to the second face of the central layer.

In still another aspect, the subject matter provides a method for reducing transmission of odorous species. The method comprises providing a multilayer film having a plurality of layers each including at least one COC. At least one of the layers includes a blend of a semi-crystalline COC and an amorphous COC. The method also comprises positioning the film between a source of odorous species and a user.

In yet another aspect, the present subject matter provides a method for reducing noise produced from flexure of a multilayer laminate including a plurality of layers each including at least one COC. The laminate defines a central plane. The method comprises arranging the plurality of layers such that a norbornene concentration in each of the plurality of layers increases toward the central plane.

In still another aspect, the subject matter provides a method for reducing noise produced from flexure of a multilayer laminate including a first barrier layer and a second barrier layer. Each barrier layer includes at least one COC. The laminate includes a central layer through which extends a central plane. The method comprises arranging the laminate such that the first barrier layer is immediately adjacent to a first face of the central layer and the second barrier layer is immediately adjacent to a second face of the central layer. The second face is oppositely directed from the first face.

As will be realized, the subject matter described herein is capable of other and different embodiments and its several details are capable of modifications in various respects, all without departing from the claimed subject matter. Accordingly, the drawings and description are to be regarded as illustrative and not restrictive.

BRIEF DESCRIPTION OF THE DRAWINGS

The appended drawings are provided to illustrate and not limit the present subject matter. The components in the drawings are not to scale with emphasis instead to illustrating the principles of the subject matter.

DETAILED DESCRIPTION OF THE EMBODIMENTS

Figure 1:
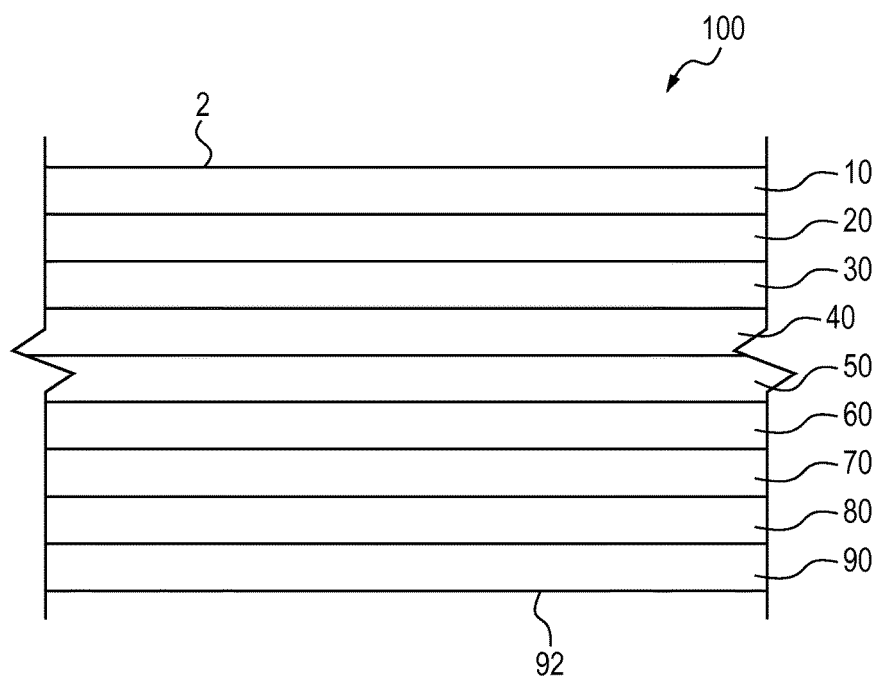
FIG. 1 is a schematic cross sectional view of a preferred embodiment multilayer polymeric film according to the present subject matter.

Generally, in accordance with the present subject matter, various preferred embodiment single and multilayer films have been identified that can be used in a wide range of applications and particularly ostomy applications.

The preferred embodiment barrier films and/or multilayer barrier assemblies are preferably halogen-free and are particularly well suited for medical applications such as forming ostomy pouches. Since the films and multilayer assemblies are halogen-free and particularly free of chlorine, they can be recycled and/or subjected to a wide array of material reclamation operations. In addition, the unique barrier materials and combination of barrier layers and/or other functional layers as described herein are particularly well suited for use in ostomy applications. Many of the barrier films exhibit low noise characteristics. These aspects and others are all described in greater detail as follows.

Polymeric Barrier Film

In one aspect, the present subject matter provides a unique barrier film that can be utilized in a wide range of applications in which it is desired to block the transmission of odor-producing molecules, water, and/or oxygen across the thickness of a layer. Typical barrier films use water vapor transmission rate (WVTR) and oxygen transmission rate (OTR) to characterize their barrier properties. Materials known to have good barrier properties against water and oxygen permeation have a high modulus, and thereby are "noisy". A goal of the present subject matter is to prevent the passage of hydrogen sulfide and other malodorous molecules and/or species. The solution may not require the same approach needed for achieving low WVTR and OTR.

In a preferred embodiment of the present subject matter, a polymeric barrier film is provided which comprises at least one layer comprising a semi-crystalline cyclic olefin copolymer (COC). Cyclic olefin copolymers are also known as cyclo ethylene copolymer, COC, cyclo olefin copolymer, cyclic olefin polymer, and ethylene-norbornene copolymer. The terms "cyclic olefin copolymer" or "COC" are used interchangeably herein and include these various terms of art. It is contemplated that in certain embodiments, various norbornene-based materials may be used instead of or in addition to the COC's, as described in greater detail herein. And, in particular embodiments, an elastomeric COC is used. In other embodiments, it is preferred to utilize blends of one or more of these COCs and optionally with other materials such as polyolefins, tie components, and/or amorphous COCs as described in greater detail herein.

Presently, there exist numerous grades of commercially available cyclic olefin copolymers based on different types of cyclic monomers and polymerization methods. Cyclic olefin copolymers are typically produced by chain copolymerization of cyclic monomers such as 8,9,10-trinorborn-2-ene (norbornene) or 1,2,3,4,4a,5,8,8a-octahydro-1,4:5,8-dimethanonaphthalene (tetracyclododecene) with ethene. Non-limiting examples of commercially available cyclic olefin copolymers include those available from TOPAS Advanced Polymers under the designation TOPAS, Mitsui Chemical's APEL, or those formed by ring-opening metathesis polymerization of various cyclic monomers followed by hydrogenation, which are available from Japan Synthetic Rubber under the designation ARTON, and Zeon Chemical's ZEONEX and ZEONOR.

In accordance with the present subject matter, a barrier layer comprising a semi-crystalline COC is provided. In other preferred embodiments, a combination of COCs is used in one or more barrier layers. Most preferably, the combination of COCs includes a semi-crystalline COC and one or more amorphous COCs. However, the subject matter includes a combination of two or more semi-crystalline COCs and optionally further combined with one or more amorphous COCs.

Preferably in certain embodiments, the semi-crystalline COC has a melting temperature (Tm) of from about 70° C. to about 120° C., more preferably from about 75° C. to about 110° C., and most preferably from about 80° C. to about 100° C. Preferably, the semi-crystalline COC has a glass transition temperature (Tg) of from about −20° C. to about 20° C., more preferably from about −19° C. to about 15° C., and most preferably from about −17° C. to about 10° C.

Preferably, the semi-crystalline COC has a norbornene content of from about 5% to about 25%, more preferably from about 10% to about 20%, and most preferably from about 12% to about 18% by mole. These molar concentrations are based upon the amount of the semi-crystalline COC. In certain embodiments it is preferred to utilize a semi-crystalline COC having a norbornene content of less than 20%. In certain embodiments, it is preferred to utilize a semi-crystalline COC having a particular degree of crystallinity. For example, in certain applications it is preferred to use a semi-crystalline COC having a crystallinity of 5% or more by weight. In other applications, it is preferred to utilize a semi-crystalline COC having a crystallinity of 10% or more by weight. And in still other embodiments, it is preferred to use a semi-crystalline COC having a crystallinity of 20% or more by weight.

Preferably, in certain embodiments, the barrier film comprises a blend of cyclic olefin copolymers (COC) in which the blend includes a semi-crystalline cyclic olefin copolymer (COC) and the total norbornene concentration in the barrier film is from about 12 mole % to about 60 mole %, more preferably from about 15 mole % to about 55 mole %, and most preferably from about 18 mole % to about 50 mole %. These molar concentrations are based upon the total amounts of COCs in the blend or layer of interest.

A most preferred semi-crystalline COC is commercially available under the designation E-140 from TOPAS. The melting temperature of the E-140 grade is about 84° C. and has a Vicat softening temperature of about 64° C. The glass transition temperature of the E-140 grade is about 6° C. The norbornene comonomer content of the E-140 grade is believed to be about 12% to about 18%. Details and property information regarding the E-140 grade are set forth below in Table 1.

TABLE 1

| Grade E-140 Cyclic Olefin Copolymer From TOPAS | | | |
|---|---|---|---|
| Property | Value | Unit | Test Standard |
| Physical Properties | | | |
| Density | 0.940 | g/cm$^3$ | ISO 1183 |
| Melt volume rate (MVR) at 190° C. and 2.16 kg | 3.0 | cm$^3$/10 min | ISO 1133 |
| Melt volume rate (MVR) at 260° C. and 2.16 kg | 12.0 | cm$^3$/10 min | ISO 1133 |
| Hardness, shore A | 89 | — | ISO 868 |
| WVTR (23° C./85% RH) | 1.0 | g*100 μm/m$^2$ *day | ISO 15106-3 |
| WVTR (38° C./90% RH) | 4.6 | g*100 μm/m$^2$ *day | ISO 15106-3 |
| OTR (23° C./50% RH) | 1060 | cc*100 μm/m$^2$ *day | ISO 15105-2 |
| Mechanical Properties | | | |
| Tensile stress at break (50 mm/min) | >19 | MPa | ISO 527-T2/1A |
| Tensile modulus (1 mm/min) | 44 | MPa | ISO 527-T2/1A |
| Tensile strain at break (50 mm/min) | >450 | % | ISO 527-T2/1A |
| Compression set (24 hr/23° C.) | 35 | % | ISO 815 |
| Compression set (72 hr/23° C.) | 32 | % | ISO 815 |
| Compression set (24 hr/60° C.) | 90 | % | ISO 815 |
| Tear strength | 47 | kN/m | ISO 34-1 |
| Puncture resistance | 44 | J | ASTM D3786-08 |
| Film Properties - 50 μm/2 mil cast film | | | |
| Tensile stress at break (machine direction) | 8.8 | ksi | ASTM D882 |
| Tensile modulus (MD) | 5.26 | ksi | ASTM D882 |
| Elongation at break (MD) | 640 | % | ASTM D882 |
| Tensile stress at break (transverse direction) | 7.31 | ksi | ASTM D882 |
| Tensile modulus (TD) | 4.93 | Ksi | ASTM D882 |
| Elongation at break (TD) | 620 | % | ASTM D882 |
| Elmendorf tear (MD, 3200 grams) | 1103 | grams | ASTM D1922 |
| Elmendorf tear (TD, 3200 grams) | 1221 | grams | ASTM D1922 |
| Haze | 1.5 | % | ASTM D1003 |
| Gloss (60° C.) | 94 | % | ASTM D2457 |
| Electrical Properties | | | |
| Relative permittivity at 1 GHz | 2.24 | — | ASTM D2520/B |
| Dissipation factor at 1 GHz | 2.6E−04 | — | ASTM D2520/B |
| Dielectric strength | 4000 | V/mil | ASTM D149-97a |
| Thermal Properties | | | |
| Ductile-brittle temperature | <−90 | ° C. | ISO 974 |
| Tm - melt temperature | 84 | ° C. | Internal method |
| Vicat softening temperature, VST/A50 | 64 | ° C. | ISO 306 |

As noted, in certain embodiments, it may be preferred to combine one or more semi-crystalline COCs with one or more amorphous COCs. The preferred amorphous COCs have a Tg of from about 33° C. to about 180° C., more preferably from about 45° C. to about 130° C., and most preferably from about 60° C. to about 80° C. Preferred amorphous COCs which are commercially available include grades 9506 and 8007, and particularly grade 8007F-04 from TOPAS. Details and property information for these materials are set forth below in Tables 2 and 3. Additional examples of commercially available COCs which can be used in the barrier films are presented in Tables 4-6.

TABLE 2

Grade 9506 Cyclic Olefin Copolymer From TOPAS

| Property | Value | Unit | Test Standard |
|---|---|---|---|
| Physical Properties | | | |
| Density | 1020 | kg/m$^3$ | ISO 1183 |
| Melt volume rate (MVR) | 6.0 | cm$^3$/10 min | ISO 1133 |
| MVR test temperature | 230 | ° C. | ISO 1133 |
| MVR test load | 2.16 | Kg | ISO 1133 |
| Melt volume rate (MVR) - 2nd value | 1.0 | cm$^3$/10 min | ISO 1133 |
| MVR test temperature - 2nd value | 190 | ° C. | ISO 1133 |
| MVR test load - 2nd value | 2.16 | Kg | ISO 1133 |
| Water absorption (23° C.-sat) | 0.01 | % | ISO 62 |
| Thermal Properties | | | |
| Glass transition temperature 10° C./min | 65 | ° C. | ISO 11357-1, -2, -3 |
| Mechanical Properties (Film) | | | |
| Tensile modulus (machine direction) | 1700 | MPa | ISO 527-3 |
| Tensile modulus (transverse direction | 2000 | MPa | ISO 527-3 |
| Tensile strength @ break (machine direction) | 55 | MPa | ISO 527-3 |
| Tensile strength @ break (transverse direction) | 55 | MPa | ISO 527-3 |
| Elongation at break (machine direction) | 2.9 | % | ISO 527-3 |
| Elongation at break (transverse direction) | 3.6 | % | ISO 527-3 |
| Elmendorf tear strength (machine direction) | 230 | G | ISO 6383-2 |
| Elmendorf tear strength (transverse direction) | 240 | G | ISO 6383-2 |
| Dart Drop Impact Strength, F50 | <36 | G | ISO 7765-1 |
| Optical Properties (Film) | | | |
| Gloss, 60° | >100 | % | ISO 2813 |
| Haze | <1 | % | ISO 14782 |
| Barrier Properties (Film) | | | |
| Water vapor permeability @ 38° C., 90% RH | 0.8 | g · 100 μm/(m$^2$ · day) | ISO 15106-3 |
| Oxygen Permeability @ 23° C., 50% RH | 170.0 | cm$^3$ · 100 μm/(m$^2$ · day · bar) | ASTM D3985 |

TABLE 3

Grade 8007F-04 Cyclic Olefin Copolymer From TOPAS

| Property | Value | Unit | Test Standard |
|---|---|---|---|
| Physical Properties | | | |
| Density | 1020 | kg/m$^3$ | ISO 1183 |
| Melt volume rate (MVR) | 12.0 | cm$^3$/10 min | ISO 1133 |
| MVR test temperature | 230 | ° C. | ISO 1133 |
| MVR test load | 2.16 | Kg | ISO 1133 |
| Melt volume rate (MVR) - 2nd value | 2.0 | cm$^3$/10 min | ISO 1133 |
| MVR test temperature - 2nd value | 190 | ° C. | ISO 1133 |
| MVR test load - 2nd value | 2.16 | Kg | ISO 1133 |
| Water absorption (23° C.-sat) | 0.01 | % | ISO 62 |
| Thermal Properties | | | |
| Glass transition temperature 10° C./min | 78 | ° C. | ISO 11357-1, -2, -3 |
| Mechanical Properties (Film) | | | |
| Tensile modulus (machine direction) | 2200 | MPa | ISO 527-3 |
| Tensile modulus (transverse direction) | 1800 | MPa | ISO 527-3 |
| Tensile strength @ break (machine direction) | 57 | MPa | ISO 527-3 |
| Tensile strength @ break (transverse direction) | 50 | MPa | ISO 527-3 |
| Elongation at break (machine direction) | 2.9 | % | ISO 527-3 |
| Elongation at break (transverse direction) | 3.0 | % | ISO 527-3 |
| Elmendorf tear strength (machine direction) | 225 | G | ISO 6383-2 |
| Elmendorf tear strength (transverse direction) | 230 | G | ISO 6383-2 |
| Dart Drop Impact Strength, F50 | <36 | G | ISO 7765-1 |

TABLE 3-continued

Grade 8007F-04 Cyclic Olefin Copolymer From TOPAS

| Property | Value | Unit | Test Standard |
|---|---|---|---|
| Optical Properties (Film) | | | |
| Gloss, 60° | >100 | % | ISO 2813 |
| Haze | <1 | % | ISO 14782 |
| Barrier Properties (Film) | | | |
| Water vapor permeability @ 38° C., 90% RH | 0.8 | g · 100 μm/(m$^2$ · day) | ISO 15106-3 |
| Oxygen Permeability @ 23° C., 50% RH | 200.0 | cm$^3$ · 100 μm/(m$^2$ · day · bar) | ASTM D3985 |

TABLE 4

Grade 6017S-04 Cyclic Olefin Copolymer from TOPAS

| Property | Value | Unit | Test Standard |
|---|---|---|---|
| Physical Properties | | | |
| Density | 1020 | kg/m$^3$ | ISO 1183 |
| Melt volume rate (MVR) | 1.5 | cm$^3$/10 min | ISO 1133 |
| MVR test temperature | 260 | ° C. | ISO 1133 |
| MVR test load | 2.16 | kg | ISO 1133 |
| Water absorption (23° C.-sat) | 0.01 | % | ISO 62 |
| Mechanical Properties | | | |
| Tensile modulus (1 mm/min) | 3000 | MPa | ISO 527-2/1A |
| Tensile stress at break (5 mm/min) | 58 | MPa | ISO 527-2/1A |
| Tensile strain at break (5 mm/min) | 2.4 | % | ISO 527-2/1A |
| Charpy impact strength @ 23° C. | 15 | KJ/m$^2$ | ISO 179/1eU |
| Charpy notched impact strength @ 23° C. | 1.6 | KJ/m$^2$ | ISO 179/1eA |
| Thermal Properties | | | |
| Glass transition temperature (10° C./min) | 178 | ° C. | ISO 11357-1, -2, -3 |
| DTUL @ 0.45 MPA | 170 | ° C. | ISO 75-1, -2 |
| Vicat softening temperature B50 (50° C./h 50N) | 178 | ° C. | ISO 306 |
| Flammability @ 1.6 mm nom. thickn. | HB | Class | UL94 |
| thickness tested (1.6) | 1.6 | mm | UL94 |
| UL recognition (1.6) | UL | — | UL94 |
| Electrical Properties | | | |
| Relative permittivity at 1-10 kHz | 2.35 | — | IEC 60250 |
| Relative permittivity at 1 GHz | 2.3 | — | IEC 60250 |
| Dissipation factor at 1 GHz | 7.0E−05 | — | IEC 60250 |
| Volume restivity | >1E14 | ohm-m | IEC 60093 |
| Comparative tracking index CTI | >600 | — | IEC 60112 |
| Optical Properties | | | |
| Deg. of light transmission | 91 | % | ISO 13468-2 |
| Refractive index | 1.53 | — | ISO 489 |

TABLE 5

Grade 6015S-04 Cyclic Olefin Copolymer from TOPAS

| Property | Value | Unit | Test Standard |
|---|---|---|---|
| Physical Properties | | | |
| Density | 1020 | kg/m$^3$ | ISO 1183 |
| Melt volume rate (MVR) | 4.0 | cm$^3$/10 min | ISO 1133 |
| MVR test temperature | 260 | ° C. | ISO 1133 |
| MVR test load | 2.16 | kg | ISO 1133 |
| Water absorption (23° C.-sat) | 0.01 | % | ISO 62 |
| Mechanical Properties | | | |
| Tensile modulus (1 mm/min) | 3000 | MPa | ISO 527-2/1A |
| Tensile stress at break (5 mm/min) | 60 | Mpa | ISO 527-2/1A |
| Tensile strain at break (5 mm/min) | 2.5 | % | ISO 527-2/1A |
| Charpy impact strength @ 23° C. | 15 | KJ/m$^2$ | ISO 179/1eU |
| Charpy notched impact strength @ 23° C. | 1.6 | KJ/m$^2$ | ISO 179/1eA |

TABLE 5-continued

Grade 6015S-04 Cyclic Olefin Copolymer from TOPAS

| Property | Value | Unit | Test Standard |
|---|---|---|---|
| Thermal Properties | | | |
| Glass transition temperature (10° C./min) | 158 | ° C. | ISO 11357-1, -2, -3 |
| DTUL @ 0.45 MPA | 150 | ° C. | ISO 75-1, -2 |
| Vicat softening temperature B50 (50° C./h 50N) | 156 | ° C. | ISO 306 |
| Flammability @ 1.6 mm nom. thickn. | HB | Class | UL94 |
| thickness tested (1.6) | 1.6 | mm | UL94 |
| UL recognition (1.6) | UL | — | UL94 |
| Electrical Properties | | | |
| Relative permittivity at 1-10 kHz | 2.35 | — | IEC 60250 |
| Relative permittivity at 1 GHz | 2.3 | — | IEC 60250 |
| Dissipation factor at 1 GHz | 7.0E−05 | — | IEC 60250 |
| Volume restivity | >1E14 | ohm-m | IEC 60093 |
| Comparative tracking index CTI | >600 | — | IEC 60112 |
| Optical Properties | | | |
| Deg. of light transmission | 91 | % | ISO 13468-2 |
| Refractive index | 1.53 | — | ISO 489 |

TABLE 6

Grade 5013X14 Cyclic Olefin Copolymer from TOPAS

| Property | Value | Unit | Test Standard |
|---|---|---|---|
| Physical Properties | | | |
| Density | 1020 | kg/m$^3$ | ISO 1183 |
| Melt volume rate (MVR) | 9.0 | cm$^3$/10 min | ISO 1133 |
| MVR test temperature | 230 | ° C. | ISO 1133 |
| MVR test load | 2.16 | kg | ISO 1133 |
| Melt volume rate (MVR) - 2$^{nd}$ value | <0.1 | cm$^3$/10 min | ISO 1133 |
| MVR test temperature - 2$^{nd}$ value | 190 | ° C. | ISO 1133 |
| MVR test load - 2$^{nd}$ value | 2.16 | kg | ISO 1133 |
| Water absorption (23° C.-sat) | 0.01 | % | ISO 62 |
| Thermal Properties | | | |
| Glass transition temperature (10° C./min) | 134 | ° C. | ISO 11357-1, -2, -3 |
| Mechanical Properties (Film) | | | |
| Tensile modulus (machine direction) | 2600 | MPa | ISO 527-3 |
| Tensile modulus (transverse direction) | 2500 | MPa | ISO 527-3 |
| Tensile strength @ break (machine direction) | 35 | MPA | ISO 527-3 |
| Tensile strength @ break (transverse direction) | 25 | MPa | ISO 527-3 |
| Elongation at break (machine direction) | 1.4 | % | ISO 527-3 |
| Elongation at break (transverse direction) | 1.1 | % | ISO 527-3 |
| Elmendorf tear strength (machine direction) | 11 | g | ISO 6383-2 |
| Elmendorf tear strength (transverse direction) | 11 | g | ISO 6383-2 |
| Dart Drop Impact Strength, F50 | <36 | g | ISO 7765-1 |
| Optical Properties (Film) | | | |
| Gloss, 60° C. | >100 | % | ISO 2813 |
| Haze | <1 | % | ISO 14782 |
| Barrier Properties (Film) | | | |
| Water vapor permeability @ 38° C., 90% RH | 1.0 | g-100 μm/(m$^2$-day) | ISO 15106-3 |
| Oxygen Permeability @ 23° C., 50% RH | 250.0 | cm$^3$-100 μm/(m$^2$-day-bar) | ASTM D3985 |
| Test Specimen Production (Film) | | | |
| Type of extrusion | cast | | |
| Thickness of specimen | 0.07 | mm | |

If one or more amorphous COCs are used in combination with the semi-crystalline COC, it is preferred that the weight proportion of the semi-crystalline COC range from about 1% to about 99%, more preferably from about 5% to about 75%, and most preferably from about 5% to about 50%, based upon the total weight amount of COC's in the barrier layer. However, it will be appreciated that the subject matter includes barrier layers with less than 1% semi-crystalline COC, and greater than 99% semi-crystalline COC.

For certain applications, it may be preferred to utilize a COC having elastomeric properties. As will be appreciated, elastomers exhibit a property of viscoelasticity or as commonly referred, elasticity. Elastomers typically have a relatively low Young's modulus and a high yield strain as compared to most other materials. It is contemplated that an elastomeric COC could be used in the various embodiments described herein. Reported information for an elastomeric COC from TOPAS indicates that the COC elastomers have a tensile modulus of about 4,412 N/cm$^2$ and elongation at break greater than 450%. In addition, the elastomeric COC exhibits relatively low dielectric properties comparable to certain fluoroelastomers, thereby providing excellent electrical insulation performance. Furthermore, the material is reported to maintain ductility at temperatures below −80° C. The noted elastomeric COC also reportedly exhibits a Shore A hardness of 89.

In certain other embodiments, it is preferred to utilize ethylene vinyl alcohol (EVOH) in the polymeric barrier film. Specifically, the EVOH may be incorporated in the layer(s) comprising COC, and/or be provided in one or more separate layers proximate the COC-containing layer(s) in the barrier film. Ethylene vinyl alcohol, commonly abbreviated EVOH, is a formal copolymer of ethylene and vinyl alcohol. Because the latter monomer mainly exists as its tautomer acetaldehyde, the copolymer is prepared by polymerization of ethylene and vinyl acetate to produce the ethylene vinyl acetate (EVA) copolymer followed by hydrolysis. EVOH is typically used to provide barrier properties, primarily as an oxygen barrier for improved food packaging shelf life and as a hydrocarbon barrier for fuel tanks. EVOH is typically coextruded or laminated as a thin layer between cardboard, foil, or other plastics. EVOH copolymer is traditionally defined by the mole percent ethylene content. Lower ethylene content grades have higher barrier properties, and higher ethylene content grades have lower temperatures for extrusion. Additional information as to preferred aspects of EVOH used in the films of the subject matter are described in greater detail herein.

Multilayer Barrier

The present subject matter also provides multilayer films for use in medical applications and in particular, for ostomy applications. As will be appreciated, an important characteristic for such films is preventing or at least significantly reducing transmission of odors through the film, and particularly reducing transmission of skatole or 3-methylindole through the film. Another important characteristic for such films is that the films be relatively quiet and not emit excessive noise upon deflecting or movement of the film. A preferred multilayer barrier construction uses one or more barrier layers that include a semi-crystalline cyclic olefin copolymer (COC) and in combination with one or more flexible support layers. Another preferred multilayer barrier construction includes one or more barrier layers that include ethylene vinyl alcohol in conjunction with one or more layers which include a semi-crystalline COC. In other embodiments, the preferred multilayer barrier construction includes one or more of the previously noted aspects in further combination with an inner layer containing one or more antimicrobial agents.

Certain multilayer barrier films of the present subject matter are generally as set forth below.

TABLE 7

Preferred Embodiment Barrier Film

| Layer | Description | Thickness |
|---|---|---|
| A | RF Weldable Polymers, up to 20% Antiblock, and Slip Masterbatch | 5-20% |

TABLE 7-continued

Preferred Embodiment Barrier Film

| Layer | Description | Thickness |
|---|---|---|
| B | At least one Polyolefin Elastomer or Blends Thereof | 0-25% |
| C | At least one Polyolefin Elastomer or Blends Thereof | 0-25% |
| D | Blends of COC with up to 20% tie component; Preferably Blends Comprising 50%-75% TOPAS 8007 and 50%-25% TOPAS E-140 (weight percent) | 4-12% |
| E | EVOH; Preferably 38%-48% (mole percent) grade | 5-10% |
| F | Blends of COC with up to 20% tie component; Preferably Blends Comprising 50%-75% TOPAS 8007 and 50%-25% TOPAS E-140 (weight percent) | 4-12% |
| G | At least one Polyolefin Elastomer or Blends Thereof | 0-25% |
| H | Blends of materials of Layer G and Layer I in a ratio of from 50% to 80% (by weight) of Layer I; and optionally up to 20% of tie component | 5-30% |
| I | RF Weldable Polymers, up to 20% Antiblock, and Slip Masterbatch, and up to 20% Antimicrobial Masterbatch | 5-30% |

TABLE 8

Preferred Embodiment Barrier Film

| Layer | Description | Thickness |
|---|---|---|
| A | RF Weldable Polymers, up to 20% Antiblock, and Slip Masterbatch | 5-20% |
| B | At least one Polyolefin Elastomer or Blends Thereof | 0-25% |
| C | At least one Polyolefin Elastomer or Blends Thereof | 0-25% |
| D | Blends of COC with up to 20% tie component; Preferably blends comprising 75%-95% TOPAS 9506 and 25%-5% TOPAS E-140 (weight percent) | 4-12% |
| E | EVOH; Preferably 38%-48% (mole percent) grade | 5-10% |
| F | Blends of COC with up to 20% tie component; Preferably blends comprising 75%-95% TOPAS 9506 and 25%-5% TOPAS E-140 (weight percent) | 4-12% |
| G | At least one Polyolefin Elastomer or Blends Thereof | 0-25% |
| H | Blends of materials of Layer G and Layer I in a ratio of from 50% to 80% (by weight) of Layer I; and optionally up to 20% of tie component | 5-30% |
| I | RF Weldable Polymers, up to 20% Antiblock, and Slip Masterbatch, and up to 20% Antimicrobial Masterbatch | 5-30% |

TABLE 9

Preferred Embodiment Barrier Film

| Layer | Description | Thickness |
|---|---|---|
| A | RF Weldable Polymers, up to 20% Antiblock, and Slip Masterbatch | 5-20% |
| B | At least one Polyolefin Elastomer or Blends Thereof | 0-25% |
| C | At least one Polyolefin Elastomer or Blends Thereof | 0-25% |
| D | Blends of COC with up to 20% tie component; Preferably blends comprising 75%-95% TOPAS 8007 and 25%-5% TOPAS E-140 (weight percent) | 4-12% |
| E | EVOH; Preferably 38%-48% (mole percent) grade | 5-10% |
| F | Blends of COC with up to 20% tie component; Preferably blends comprising 75%-95% TOPAS 8007 and 25%-5% TOPAS E-140 (weight percent) | 4-12% |
| G | At least one Polyolefin Elastomer or Blends Thereof | 0-25% |
| H | Blends of materials of Layer G and Layer I in a ratio of from 50% to 80% (by weight) of Layer I; and optionally up to 20% of tie component | 5-30% |
| I | RF Weldable Polymers, up to 20% Antiblock, and Slip Masterbatch, and up to 20% Antimicrobial Masterbatch | 5-30% |

The only difference between the preferred embodiment barrier films of Tables 7, 8 and 9 is the composition of layers D and F which contain blends of COCs.

Layer A is the outermost layer and preferably comprises ethylene vinyl acetate (EVA) having a vinyl acetate molar content of 12% to 28%. Layer A also contains a masterbatch of slip and antiblock agents. The masterbatch preferably is SAB1220 NG masterbatch (A. Schulmann product) added at 20% by weight. The masterbatch contains 8% slip and 12% antiblock agents. In certain embodiments, layer A may be provided in a nonwoven form. Layer A is preferably comprised of polymeric materials suitable for welding and particularly for RF welding. Examples of RF weldable polymers include but are not limited to ethylene vinyl acetate (EVA) and ethylene butyl acrylate (EBA)

Layer B comprises one or more polyolefin elastomers. Examples of preferred polyolefin elastomers include but are not limited to VERSIFY 2300, VERSIFY DE2400, ENGAGE 8150, AFFINITY 8100G, INFUSE 9000, NOTIO P, and/or VISTAMAXX or blends thereof. Additional representative examples of suitable polyolefin elastomers are provided herein. VERSIFY 2300 is a polyolefin elastomer (POE), and specifically, a propylene-ethylene copolymer available from Dow Chemical. AFFINITY 8100G is a polyolefin elastomer and is believed to be a saturated ethylene-octene copolymer, and is available from Dow Chemical. INFUSE 9000 is an olefin block copolymer and is believed to be an ethylene-octene block copolymer, and is available from Dow Chemical.

Layers C and G each comprises one or more polyolefin elastomers. Preferably, the material of Layers C and G is selected so as to match the material of layer B. Thus, if layer B is VERSIFY 2300, then the material for layers C and G is also VERSIFY 2300. Alternatively, if layer B is INFUSE 9000, then the material for layers C and G is also INFUSE 9000. However, it will be appreciated that the subject matter includes the use of other polyolefin elastomers in one or both of layers C and G which are different than the polyolefin elastomer(s) used in layer B.

Each of layers D and F contains an amorphous COC. Layers D and F primarily function as odor barrier layers. Preferably, two grades of amorphous COC from TOPAS, grade 9506F and/or grade 8007, may be used. The Tg of grade 8007 is believed to be 78° C. The Tg of grade 9506 is believed to be 65° C. In the preferred embodiment barrier films, a semi-crystalline COC elastomer is used, and is available from TOPAS under the designation E-140. The E-140 COC has a density of 0.94 g/cm$^3$ and a comonomer content of about 12% norbornene. The melting point of the E-140 material is about 84° C. and the material has a glass transition temperature of about 6° C. An effective amount of a tie component can be used in each of these layers. The tie material is preferably BYNEL E418, available from DuPont. That material is described as anhydride-modified EVA, and is believed to be maleic anhydride grafted EVA polymer.

Layer E is ethylene vinyl alcohol (EVOH) available from EVAL Americas, a business unit of Kuraray. Preferably, the EVOH used in layer E includes 25 to 50 mole % ethylene, more preferably, 32 to 48 mole % ethylene, and most preferably 38 to 44 mole % ethylene. Examples of suitable grades of EVOH include but are not limited to SP292 or E-171 available from Kuraray.

Layer H preferably comprises a blend of materials used in layers G and I, and optionally up to 20% by weight of a tie component. The blend of materials G and I can be prepared by combining the materials used in those layers in a weight ratio of from about 1:99 to about 99:1, respectively. The total amount of the materials used in layer H is preferably from 50% to 80% by weight of the weight of layer I.

Layer I preferably comprises one or more polymeric materials suitable for welding and particularly for RF welding. Examples of RF weldable polymers include those described in conjunction with layer A. Layer I may also comprise up to 20% of one or more antimicrobial agents and typically provided in the form of an antimicrobial masterbatch.

The preferred embodiment film constructions are believed to exhibit several advantages over currently known ostomy films. The preferred films are halogen-free and avoid the use of polyvinylidene chloride (PVDC). The preferred films are quieter and exhibit significantly less "rustle". And, the preferred films appear to exhibit superior odor blocking characteristics. The film constructions may be transparent or contain coloring agents.

FIG. 1 is a schematic illustration of a preferred embodiment multilayer barrier assembly 100 in accordance with the present subject matter. The multilayer assembly 100 comprises an outer layer 10 defining an outer face 2, a first flexible support layer 20, a second flexible support layer 30, a first moisture and odor barrier layer 40, a secondary barrier layer 50 for reducing transmission of oxygen, a second moisture and odor barrier layer 60, a third flexible support layer 70, a fourth flexible support layer 80, and an inner antimicrobial layer 90 defining an inner face 92 for contacting a microbe containing medium. Tables 7-9 describe preferred embodiment multilayer films and properties and materials for each of the layers 10, 20, 30, 40, 50, 60, 70, 80, and 90. These layers are designated as layers A, B, C, D, E, F, G, H, and I respectively in Tables 7-9.

The total thickness of the preferred multilayer films is 2 mils or greater.

Referring again to FIG. 1, layer 10 is the outermost layer and preferably comprises ethylene vinyl acetate (EVA) having a vinyl acetate content of preferably about 18% or blends of 50% of EBA 30% and 50% of EVA (12 to 28 mole %). Layer 10 also optionally contains a masterbatch of slip and antiblock (AB) agents. The masterbatch is preferably SAB1220 NG masterbatch available from A. Schulman, added at about 20% by weight. The masterbatch contains 8% slip and 12% antiblock agents. It will be appreciated, however, that a wide array of other slip agents and/or antiblock agents could be used. Non-limiting examples of other slip agents include primary and secondary amide slip agents, polydimethyl siloxane and its copolymers, polywax slip agents, and other like agents. Non-limiting examples of other antiblock agents include inorganic fillers such as talc, calcium carbonate, clay and the like; and polymeric agents such as low density polyethylene (LDPE), highly branched low density polyethylene, and other comparable components. In certain embodiments, effective amounts of ethylene butyl acrylate (EBA) can be included in layer 10. Optionally, an effective amount of a tie component can be used in this layer. If a tie component is used in layer 10, the material is preferably anhydride (M.A.) modified. An example of such a material is BYNEL E418, available from DuPont. That material is described as anhydride-modified EVA, and is believed to be maleic anhydride grafted EVA polymer. Another example is PLEXAR from Equistar which may include grafted M.A. HDPE, LLDPE, PS, or PP.

Layers 20, 30, 70 and 80 are each a flexible support layer. The preferred embodiment multilayer film preferably includes multiple flexible support layers. The support layers provide bulk, strength, softness, and cohesiveness to the resulting multilayer assembly. In certain multilayer configurations, the one or more flexible support layers serve to dampen noise that might otherwise be emitted upon deformation or movement of the film. These layers preferably comprise one or more polyolefins, plastomers, styrene elastomers, and/or combinations thereof. Preferably, the flexible support layers such as layers 20, 30, 70, and 80 comprise one or more polymers having a relatively low density of from about 0.75 to about 1.10 g/cm$^3$, more preferably from about 0.85 to about 1.01 g/cm$^3$, and more preferably from about 0.860 to about 0.95 g/cm$^3$. Preferably, the polyolefins in the support layers such as layers 20, 30, 70 and 80 have a melt flow index (MI) of from about 0.1 to about 1000 g/10 min, and more preferably from about 0.5 to about 100 g/10 min. Preferably, the polyolefins used in the support layer(s) such as layers 20, 30, 70, and 80, include an ethylene based polymer with one or more alkyl comonomer(s) selected from the family of propylene, butylene, hexene, octene, and the like. The polyolefin can be a random copolymer or a block copolymer. In certain embodiments, it may be preferred to utilize one or more plastomer(s) in the support layer(s) such as layers 20, 30, 70, and 80. A plastomer is a polyolefin elastomer. A preferred plastomer is a propylene based plastomer having an alkyl comonomer in the family of ethylene, butylene, hexene, octene and the like. The noted plastomer can be a random copolymer or a block copolymer.

As noted, the flexible supports in the preferred multilayer constructions utilize a low density polyolefin and preferably, a polyolefin elastomer. A wide array of commercially available polyolefin elastomers can be used for one or more of the flexible support layers. Representative preferred examples of such materials include KRATON™ D1164P and G2832 available from Kraton Polymers US, LLC of Houston, Tex.; DOW AFFINITY™ DG8200 and DOW ENGAGE™ such as EG8100 and EG8150; DOW VERSIFY™ 3200, DE2400, 2400 and 3000; and DOW INFUSE™ such as INFUSE 9000 from Dow Chemical Corp. of Midland, Mich.; DYNAF-LEX™ G2755 from GLS Corp. of McHenry, Ill.; SEPTON™ 2063 2004 AND 7311 from Kuraray of Tokyo, Japan; and VISTAMAXX™ VM1100 from ExxonMobil Chemical Co. of Houston, Tex. Another preferred commercially available material for any of layers 20, 30, 70 and/or 80 is an elastomer material available from Mitsui Chemicals under the designation NOTIO™. A preferred grade is NOTIO™ PN 2070. Table 10 set forth below presents representative modulus, tear strength, and density values for films made using various specific grades of these materials.

TABLE 10

Summary of Modulus, Tear Strength and Density

| Core Resin Name | Modulus [MPa] | | Tear Strength [g] | | Density [g/cm$^3$] |
| --- | --- | --- | --- | --- | --- |
| | MD | TD | MD | TD | |
| KRATON ™ D1164P | 40.3 | 9.6 | 95 | 776 | 0.96 |
| KRATON ™ G2832 | 5.0 | 1.7 | 179 | 207 | 1.01 |
| DOW AFFINITY ™ DG8200 | 8.8 | 8.1 | 150 | 188 | 0.93 |
| DOW AFFINITY ™ EG8100G | — | — | — | — | — |
| DYNAFLEX ™ G2755 | 9.8 | 3.2 | 175 | 186 | 0.89 |
| DOW VERSIFY ™ 3200 | 52.8 | 59.3 | 368 | 1026 | 0.93 |
| DOW VERSIFY ™ 3000 | 128.9 | 138.4 | 554 | 1205 | 0.87 |
| DOW INFUSE ™ 9000 | — | — | — | — | 0.88 |
| Kuraray SEPTON ™ 2063 | 8.0 | 8.1 | 83 | 56 | 1.00 |
| Exxon VISTAMAXX ™ VM1100 | 7.1 | 7.6 | 108 | 111 | 0.98 |
| Mitsui NOTIO ™ PN2070 | — | — | — | — | — |

Generally, a particular combination of properties is desired for the film material forming the flexible support(s) in the preferred ostomy multilayer film summarized in Tables 7-9. A relatively low modulus should contribute to lower noise. Tear strength should be relatively high. Density may also be important. Typically, preferred films exhibit a 2% secant tensile modulus of less than about 500 MPa for MD and less than about 500 MPa for TD; a spencer impact of at least about 1500 g; a tensile elongation at break greater than 200%; and a density of less than 1.1 g/cm$^3$. Preferably, preferred films exhibit a modulus of less than or equal to about 450 MPa for MD and less than or equal to about 450 MPa for TD; a spencer impact of at least or about 1000 grams; and a density of less than or equal to 1.0 g/cm$^3$. These combinations of properties for the materials forming the flexible supports, e.g. layers 20, 30, 70, and 80 in the preferred multilayer construction (i.e. layers B, C, G, and H in Tables 7-9), have been found to provide a favorable combination of properties and promote ease of processing. However, the subject matter includes the use of suitable materials exhibiting only some of these properties. It will also be understood that the subject matter includes films exhibiting different properties. For example, it is contemplated that fully formed films would exhibit modulus values less than these values, and/or spencer impact values that are greater than these values. The preferred materials of the group of commercially available materials listed in Table 10 are Exxon VISTAMAXX™ and Dow AFFINITY™, VERSIFY™, INFUSE™ and ENGAGE™. It will be appreciated that the present subject matter multilayer barrier constructions are not limited to the use of these particular elastomers.

In certain versions of the subject matter, it is preferred to utilize one or more styrenic elastomers in one or more of the support layers, such as layers 20, 30, 70, and 80 (i.e. layers B, C, G, and H in Tables 7-9). The one or more styrenic elastomers can be used exclusively or in combination with one or more polyolefins and/or polyolefin elastomers. An example of a commercially available styrenic elastomer is the previously noted SEPTON™ material. In certain embodiments, it may be preferred to incorporate acrylonitrile butadiene styrene (ABS) in one or more of the support layers.

One or more of layers 20, 30, 70 and 80 may also comprise ethylene butyl acrylate (EBA). A variety of different grades of EBA can be used, however, a commercially available grade under the designation LOTRYL 30 BA 02 from Arkema has been identified as providing desired characteristics. It is also contemplated that effective amounts of ethylene vinyl acetate (EVA) for example having a vinyl acetate content of about 18% or higher, can also be included in one or more of the layers 20, 30, 70, and 80. Although EBA or other acrylate, or EVA can be incorporated in any of the layers 20, 30, 70 and/or 80, it is preferred to incorporate EBA in layer 80. If EBA or EVA is incorporated in one or more layers such as layer 80, it is preferred to incorporate the EVA or EBA at a weight ratio of about 99% to about 50% with from about 1% to about 50% of polyolefin elastomer(s), i.e. plastomer(s). Most preferably, if EBA or EVA is used in layer 80, it is preferred to utilize about 60% of that material based upon the total weight of components in that layer.

In addition, one or more of layers 20, 30, 70 and 80 may also comprise a tie component. The tie component may be as previously described, and is preferably BYNEL CXA 410E710 from DuPont. Although the subject matter is not limited to any particular concentration of the tie component in any of the noted layers, a proportion of up to about 20% based upon the total weight of the respective layer is useful. As noted in Tables 7-9, in certain embodiments it is particularly preferred to include about 20% of a tie component in certain layers.

The barrier layer 50 is primarily for reducing transmission of oxygen and/or water, preferably comprises EVOH. The EVOH is incorporated at nearly any effective concentration, however typical concentrations range from about 40% to about 100%, preferably from about 50% to about 80%, and most preferably from about 60% to about 70%. In the preferred embodiment multilayer assembly of Tables 7-9, layer E includes 100% of EVOH. Layer 50 in FIG. 1 and/or layer E in Tables 7-9 preferably comprises ethylene vinyl alcohol (EVOH) SP292, E171, and/or G176 available from Eval Americas (also known as Kuraray). The EVOH preferably has an ethylene content of from about 25% to about 50%, more preferably from about 32% to about 48%, and most preferably from about 34% to about 48%. In the embodiment detailed in Tables 7-9, the EVOH used in layer E has an ethylene content of 44%. As will be understood, these values are molar percents, i.e., the molar proportion of ethylene in the ethylene vinyl alcohol material used. Furthermore, one or more materials such as nylons, and/or nano-filled nylon materials could be used as barrier materials. Such barrier materials could be used instead of EVOH, or in another barrier layer incorporated in the multilayer assemblies.

It is also contemplated that the barrier layer 50 may comprise one or more cyclic olefin copolymers instead of or in addition to EVOH. In certain embodiments, it may be preferred to provide an odor blocking layer that comprises one or more cyclic olefin copolymers. Although not wishing to be bound to any particular theory, it is believed that upon incorporation of a cyclic olefin copolymer, the shape of the norbornene rings in the polymeric matrix tend to trap or block odor producing molecules and/or chemical species. The use of one or more cyclic olefin copolymers in a barrier layer may be particularly desirable if water vapor transmission rate (WVTR) is not a concern for that layer.

Each of layers 40 and 60 comprises one or more semi-crystalline cyclic olefin copolymer (COC). These layers primarily function as odor barrier layers and are as previously described herein. As noted, the preferred COC is from TOPAS under the designation E-140 and has a density of 0.94 g/cc and a comonomer content of about 12% to about 18% norbornene. As previously noted, the E-140 COC is a semi-crystalline material and has a melting temperature of about 84° C., a Vicat softening point of about 64° C., and a glass transition temperature of about 6° C. It is also contemplated that four grades of amorphous COC from TOPAS, grade 9506F, 5017, 6017, and/or grade 8007, may be blended with the E-140 grade. A non-limiting representative blend ratio of semi-crystalline COC to amorphous COC is about 50/50 by weight. The Tg of grade 8007 is 78° C. The Tg of grade 9506F is 65° C. The one or more COCs can be used in the moisture or odor barrier layer in nearly any concentration, such as from about 10% to about 100%, more preferably from about 50% to about 99%, more preferably from about 65% to about 95%, more preferably from about 70% to about 90%, and most preferably about 80%. The COCs used in layers 40 and 60 may be same as one another. Alternatively, the COCs used in these layers may be different from one another.

One or both of layers 40 and 60 preferably also comprise a tie component. Preferably, the tie component is a polymeric resin. The tie component can be used at any effective concentration, such as from about 1% to about 40% by weight, preferably from about 10% to about 30% by weight, and most preferably about 20% by weight, based upon the total weight of the respective layer, such as layer 40 or layer 60. In layers 40 and 60, the tie component is preferably BYNEL CXA410E710. It is believed that this is an anhydride modified olefin.

Layer 90 is an inner layer and preferably includes one or more antimicrobial agents. In the preferred embodiment layer films listed in Tables 7-9, layer I comprises 80% EBA 30, 20% of a slip and antiblock masterbatch, and an optional effective amount of a silver ion anti-microbial masterbatch. In certain versions, the amount of the antimicrobial masterbatch is from about 8% to about 15%, and more preferably from about 10% to about 12%. As previously described with respect to layer 80; in layer 90, one or both of ethylene vinyl acetate (EVA) and/or ethylene butyl acrylate (EBA) can be used. If EVA is used, EVA having a vinyl acetate content of about 18% or higher is preferably utilized. For the embodiments shown in Tables 7-9, layer I preferably comprises 80% EBA having a butyl acrylate content of about 30%. In layer 90, 20% by weight of the SAB1220 NG masterbatch is preferably used. The SAB1220 NG masterbatch comprises slip agent(s) and antiblock agent(s) as previously described herein. In layer 90, the anti-microbial masterbatch is ABACT 422VA from A. Schulmann. However, it is also contemplated that such anti-microbial masterbatch may be substituted with BACTIBLOCK from Nanobiomatters. The Nanobiomatters antimicrobial is a silver ion on a modified organoclay. If the BACTIBLOCK masterbatch is used, in certain embodiments it is preferred to incorporate the masterbatch in the layer at a concentration of about 12%. In certain embodiments, the antimicrobial layer also preferably comprises one or more sealable polymers such as metallocene-catalyzed linear low density polyethylene (LLDPE).

The preferred embodiment multilayer barrier film described in Tables 7-9 and schematically depicted in FIG. 1, preferably utilizes each of layers 10, 20, 30, 40, 50, 60, 70, 80, and 90 (i.e. layers A, B, C, D, E, F, G, H, and I, respectively) at certain thicknesses. That is, by appropriate selection of thickness for each layer, the overall thickness of the resulting multilayer barrier is still relatively thin, yet the film exhibits excellent barrier properties. In certain embodiments, a preferred ratio of thickness for layers 10, 20, 30, 40, 50, 60, 70, 80, and 90 is 5-20/0-25/0-25/4-12/5-10/4-12/0-25/5-30/5-30, respectively. Other slight variations in thickness are contemplated. The total thickness of the three middle layers, i.e. layers 40, 50, and 60, is preferably about 34% or less of the total thickness of the multilayer film. Preferred film thickness for an ostomy application is about 70 to about 100 microns, but could be thinner or thicker.

Preferably, layers 10, 80 and 90 impart heat sealability characteristics to the resulting multilayer barrier film. Preferably, at least the materials selected for these layers render the resulting multilayer barrier film weldable and most preferably thermally weldable. Accordingly, at least a portion of the materials used in layers 80 and/or 90 are polar. This enables RF welding of the multilayer assembly. One or more polar materials such as EVA or EBA are provided in the outer layer to facilitate RF welding. However, if heat sealing or other thermal means, polar compounds may not be necessary. Instead, agents such as octene-based PE's, ULDPE (non-polar), and the like can be used.

It is also contemplated that one or more ionomers and preferably zinc ionomers can be incorporated in any of the layers of the multilayer barrier film. For the embodiments depicted in Tables 7-9, one or more ionomers can be incorporated in any of the support layers B, C, G and/or H. Preferably and in certain embodiments, one or more ionomers are included in layer H. It is also contemplated that one or more ionomers could be included in the secondary barrier layer E containing EVOH. The one or more ionomers can be used at any effective concentration. However, typically such concentrations range from about 5% to about 40%, preferably from about 10% to about 30%, and most preferably from about 15% to about 20%.

The present subject matter includes a wide array of multilayer barrier assemblies and in no way is limited to the embodiments depicted in Tables 7-9. For example, in another preferred embodiment, a multilayer barrier film is provided in which one or more support layer(s) are disposed between a COC-containing layer and a layer containing EVOH. Representative sequences of layers in accordance with preferred embodiments of the subject matter may include:

(i) COC/Support/EVOH/Support/COC,
(ii) COC/Support/EVOH/Support,
(iii) Support/EVOH/Support/COC,
(iv) COC/EVOH/Support/COC,
(v) COC/Support/EVOH/COC,
(vi) COC/Support/EVOH,
(vii) Support/EVOH/COC,
(viii) COC/EVOH/Support, and
(ix) Support/COC/EVOH.

Again, it is to be understood that in no way is the subject matter limited to any of the particular layer sequences noted herein. Moreover, it will also be appreciated that the subject matter includes one or more additional layers included or otherwise incorporated in the representative examples (i)-(ix) such as for instance, outer face layers and/or inner layers which may optionally include antimicrobial agents. The subject matter also includes multilayer assemblies having less than a total of nine layers as depicted in FIG. 1 and Tables 7-9.

As stated previously, in addition to barrier properties, it is often desirable that a polymeric barrier film not emit noise when deflected, crumpled or otherwise moved or subjected to flexure. For example, in ostomy or incontinence applications, it is desirable that the ostomy or incontinence bag not emit noise. As will be appreciated, such articles are typically worn under a user's clothing so as to hide the article from view. Films or polymeric layers that are not quiet tend to emit undesirable noise when the user undergoes motion such as when walking or sitting. In the case of the preferred embodiment multilayer barrier films, the films are significantly quieter than comparable ostomy films.

In certain versions of the present subject matter a multilayer flexible barrier film which exhibits low noise properties and adapted for use in ostomy applications is provided. The multilayer films utilize one or more barrier layers, each of which includes at least one COC or other agent including norbornene. In certain embodiments, the multilayer films utilize a particular arrangement of layers in which the norbornene concentration of the COC-containing layer increases toward the center or middle layer of the multilayer film, outward. That is, layers with a higher concentration of norbornene are disposed at or proximate the center of the multilayer film. The center of a multilayer assembly or laminate as referred to herein is a plane which bisects the laminate into two portions having equal thickness. This plane is periodically referred to herein as a "central plane". The present subject matter includes symmetrical arrangements in which an arrangement of COC-containing layers on one side of the central plane is the same as an arrangement of COC-containing layers on the other side of the central plane. The present subject matter also includes non-symmetrical arrangements of COC-containing layers in which COC-containing layers on one side and those on the other side of the central plane are different from one another or their arrangements are different from one another. The resulting multilayer films exhibit relatively low or reduced levels of noise.

In still further versions of the present subject matter, domains of immiscible elastomeric polymer can also be added to the layer(s) containing COC's or norbornene. The resulting multilayer films exhibit relatively low or reduced levels of noise.

In still additional versions of the present subject matter, a multilayer laminate is provided in which one or more layers in the laminate which include COC's and/or more particularly, norbornene; are located within the laminate assembly relatively close to the center of the laminate assembly. This strategic arrangement of norbornene-containing layers in a multilayer laminate typically results in a reduction in the distance of the norbornene-containing layer from the center of the multilayer laminate. The resulting multilayer films exhibit relatively low or reduced levels of noise.

Use of one or more of the noted strategies of (i) arranging layers in a multilayer laminate such that concentration of COC's or norbornene in the layer(s) increases in the assembly toward the center of the assembly; (ii) incorporating domains of immiscible elastomeric polymer in layers containing COC's or norbornene; and/or (iii) locating layers containing COC's or norbornene relatively close to the center of a multilayer laminate; enable reductions in the amount of COC's or norbornene in the overall laminate to achieve a given level of flexibility and/or reduced noise level associated with the laminate. That is, for a multilayer laminate having one or more layer(s) with COC's and/or norbornene, increased flexibility and/or reduced noise associated with the laminate can be achieved by one or more strategies (i)-(iii).

Any one or more of strategies (i)-(iii) can be accompanied by additional practices of reducing the thickness of layer(s) containing EVOH and/or layers containing COC's and/or norbornene. Reducing the thickness of such layers will reduce the extent of odor barrier provided by such layers. The loss in odor barrier can be compensated or supplemented by displacing all or a portion of a toughening layer containing a polyolefin elastomer such as a VERSIFY material for example, with a low modulus COC which includes a relatively elastic COC such as E-140 optionally blended with discontinuous polyolefin elastomer domains.

Another multilayer laminate embodiment of the present subject matter is presented below in Table 11.

TABLE 11

Preferred Embodiment Barrier Film

| Layer | Description | Thickness Typical | Preferred |
|---|---|---|---|
| A | RF Weldable Polymer(s), and Antiblock and Slip Agents | 8-12% | 10% |
| B | Polyolefin Elastomer(s) | 20-24% | 22% |
| C | Blend of COC(s) and Polyolefin Elastomer(s) | 8-12% | 10% |
| D | Blend of COC(s) and Polyolefin Elastomer(s) and Tie Agent | 3-7% | 5% |
| E | EVOH | 3-7% | 5% |
| F | Blend of COC(s) and Polyolefin Elastomer(s) and Tie Agent | 3-7% | 5% |
| G | Blend of COC(s) and Polyolefin Elastomer(s) | 8-12% | 10% |
| H | Blend of RF Weldable Polymer(s) and Polyolefin Elastomer(s) | 20-24% | 22% |

TABLE 11-continued

Preferred Embodiment Barrier Film

| Layer | Description | Thickness Typical | Preferred |
|---|---|---|---|
| I | RF Weldable Polymer(s) and Antiblock and Slip Agents | 9-13% | 11% |

Referring to Table 11, layer A is an outermost layer and preferably comprises a blend of 50% ethylene vinyl acetate (EVA) and 50% ethylene butyl acrylate (EBA). The EVA typically has a vinyl acetate molar content of 12% to 28%. Layer A also contains a masterbatch of slip and antiblock agents. A masterbatch containing such as previously described can be used.

Layer B is a toughening or support layer and includes a majority or entirety of one or more polyolefin elastomer(s) and in certain version, a propylene-ethylene copolymer such as the previously noted VERSIFY materials from Dow Chemical. In particular versions, the material is VERSIFY 2300. In certain versions, the at least one support layer is disposed at a distance from a central plane which is greater than the distance between the central plane and the COC-containing layer(s).

Layers C and G are each a blend of COC(s) or agent(s) containing norbornene and one or more polyolefin elastomers. The blend typically comprises a majority proportion of COC(s) and a minority proportion of polyolefin elastomers. In certain versions, the blend comprises from about 55% to about 75% COC(s) and from about 45% to about 25% polyolefin elastomer(s); and in particular, 70% COC(s) and 30% COC(s). The COC(s) can include a mixture of two or more COC's such as the previously noted grades of E-140, 9506, and 8007. A preferred mixture of COC's contains about 75% E-140 and about 25% 9506 or grade 8007. The polyolefin elastomer(s) can include any of the previously noted polyolefin elastomers such as but not limited to the VERSIFY materials.

Layer D and F is each a blend of COC(s) or agent(s) containing norbornene and one or more polyolefin elastomers. Each of the layers can also optionally include a tie agent. The layers each typically comprises a majority proportion of COC(s) and a minority proportion of polyolefin elastomers. In certain versions, the blend comprises from about 55% to about 75% COC(s) and from about 45% to about 25% polyolefin elastomer(s) and tie agent(s). In particular, each of layers D and F includes 70% of a blend of 75% grade 9506 or 8007 and 25% of grade E-140, 20% of a BYNEL tie material, and 10% polyolefin elastomer. In certain versions, each of layers D and F includes 70% of a blend of 85% grade 9506 or 8007 and 15% of grade E-140, 20% of a BYNEL tie material, and 10% polyolefin elastomer.

Layer E is ethylene vinyl alcohol (EVOH), and as previously noted, a wide array of different grades and types of EVOH can be used. Typically, the EVOH used in grade E-171 available from Kuraray.

Layer H is a blend of RF weldable polymer(s) and polyolefin elastomer(s). In certain versions, the RF weldable polymer includes a majority proportion or entirety of ethylene butyl acrylate (EBA) and a polyolefin elastomer(s) such as the previously noted VERSIFY materials. In a particular version of layer H, a blend of 70% ethylene butyl acrylate (EBA) and 30% of VERSIFY 2300 is utilized.

Layer I includes a blend of one or more RF weldable polymer(s) and optional antiblock and slip agents. In certain versions, the RF weldable polymer is ethylene butyl acrylate (EBA) and a masterbatch of antiblock and slip agents such as the previously noted SAB masterbatch is used.

Figure 3:
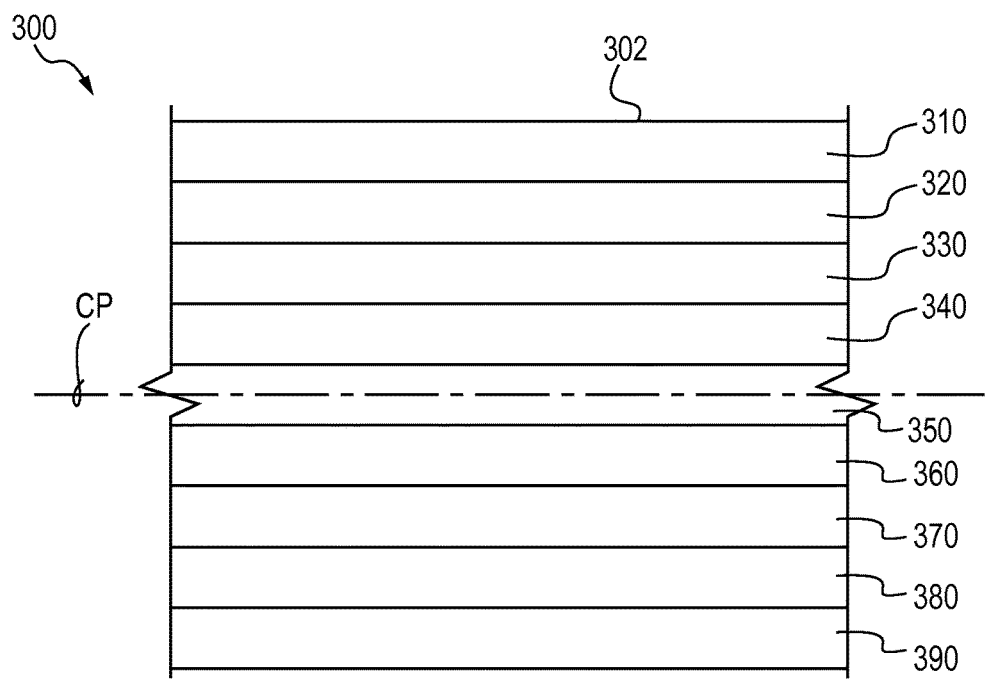
FIG. 3 is a schematic cross sectional view of another preferred embodiment multilayer polymeric film according to the present subject matter.

FIG. 3 is a schematic illustration of a preferred embodiment multilayer barrier assembly 300 in accordance with the present subject matter. The multilayer assembly 300 comprises an outer layer 310 defining an outer face 302, a first flexible support or toughening layer 320, a first moisture and odor barrier layer 330, a secondary moisture and odor barrier layer 340, an oxygen barrier 350 for reducing transmission of oxygen, a third moisture and odor barrier 360, a fourth moisture and odor barrier 370, a second flexible support or toughening layer 380, and an inner layer 390 containing an RF weldable polymer and antiblock and slip agents. The inner layer 390 may also optionally comprise one or more antimicrobial agents. FIG. 3 also illustrates a central plane CP bisecting the laminate 300 into an upper portion and a lower portion, each having an equal thickness. FIG. 3 depicts a multilayer barrier film having a plurality of layers each including at least one COC. In the particular embodiment depicted in FIG. 3, the concentration of norbornene in each layer of the plurality of layers decreases with increasing distance from the central plane. The distance is with regard to a direction transverse to the central plane. The laminate 300 includes an oxygen barrier layer 350 within which the central plane extends. The arrangement of layers in laminate 300 is such that at least one of the support layers 320, 380 is located at a distance from the central plane greater than the maximum distance between one of the plurality of layers containing COC(s) and the central plane. The multilayer laminate 300 also includes a plurality of barrier layers which include COC's and domains of immiscible elastomeric polymer. For example, layers 330, 340, 360, and 370 each include one or more COC's and one or more polyolefin elastomer(s). Preferably the polyolefin elastomer is immiscible with respect to the COC(s) and blended to result in domains of immiscible elastomeric polymer dispersed throughout the COC material or vice-versa. In a particular version of the laminate 300, each of the COC-containing layers, e.g. layers 330, 340, 360, and 370 includes a blend of a semi-crystalline COC such as the previously noted grade E-140 and an amorphous grade such as grade 9506 or 8007. In the laminate 300, the blend of COC's in the outermost layers, i.e. relative to the central plane such as 330, 370, includes a majority proportion of semi-crystalline COC's and a minority proportion of amorphous COC's. And, in the laminate 300, the blend of COC's in the innermost layers, i.e. relative to the central plane such as 340, 360, includes a majority proportion of amorphous COC's and a minority proportion of semi-crystalline COC's. In certain versions, the laminate of FIG. 3 may correspond to the construction shown in Table 11. These various features, aspects, and details of multilayer laminates provide beneficial properties and characteristics such as, but not limited to, films having low noise or "rustle" when subjected to movement or deformation, improved flexibility, overall attractive aesthetics, and improved processing aspects.

Another multilayer laminate embodiment of the present subject matter is presented below in Table 12.

TABLE 12

Preferred Embodiment Barrier Film

| Layer | Description | Thickness Typical | Thickness Preferred |
|---|---|---|---|
| A | Blend of Polyolefin Elastomer(s) and Antiblock and Slip Masterbatch | 23-27% | 25% |
| B | Blend of COC(s) and Polyolefin Elastomer(s) | 13-17% | 15% |
| C | Blend of COC(s) Polyolefin Elastomer(s), and Tie Agent | 5-9% | 7% |
| D | EVOH | 4-8% | 6% |
| E | Blend of COC(s) Polyolefin Elastomer(s), and Tie Agent | 5-9% | 7% |
| F | Blend of COC(s) and Polyolefin Elastomer(s) | 13-17% | 15% |
| G | Blend of RF Weldable Polymer(s), Polyolefin Elastomer(s) and Antiblock and Slip Masterbatch | 23-27% | 25% |

Referring to Table 12, layer A is the outermost layer and comprises a blend of polyolefin elastomer and antiblock and slip masterbatch. In certain versions, a majority proportion of polyolefin elastomer such as the previously noted VERSIFY 2300 is used and a minority proportion of antiblock and slip masterbatch is used, which is commercially available under the designation FSU-105E from A. Schulman. In particular, 80% of a polyolefin elastomer such as VERSIFY 2300 and 20% of FSU-105E is used.

Layers B and F are each a blend of COC(s) or agents containing norbornene and one or more polyolefin elastomers. The blend typically comprises a majority proportion of COC(s) and a minority proportion of polyolefin elastomers. Layers B and F of Table 12 generally correspond to previously described layers C and G of Table 11.

Layers C and E are each a blend of COC(s) or agents containing norbornene and one or more polyolefin elastomers. Each of the layers typically comprises a majority proportion of COC(s) and a minority proportion of polyolefin elastomers. Each of the layers can also include a tie agent. In certain versions, the blend comprises from about 55% to about 75% COC(s) and from about 45% to about 25% polyolefin elastomer(s) and tie agent(s). In particular, each of layers C and E includes 70% of a blend of 75 to 85% grade 9506 or 8007 and 15 to 25% of grade E140, 20% of a BYNEL tie material, and 10% polyolefin elastomer. Layers C and E generally correspond to the previously described layers D and F of Table 11.

Layer D of Table 12 is ethylene vinyl alcohol (EVOH) and is as previously described layer E of Table 11.

Layer G includes a blend of one or more RF weldable polymer(s), polyolefin elastomer(s), and antiblock and slip masterbatch which can be FSU-105E. In certain versions, layer G includes a blend of 80% of an RF weldable polymer and a polyolefin elastomer and 20% of antiblock and slip masterbatch which can be FSU-105E. The RF weldable polymer can for example be ethylene butyl acrylate (EBA) and the polyolefin elastomer can be the previously noted VERSIFY material. The proportions of RF weldable polymer and polyolefin elastomer can be any suitable proportions. A proportion of 70% RF weldable polymer and 30% polyolefin elastomer can be used.

Figure 4:
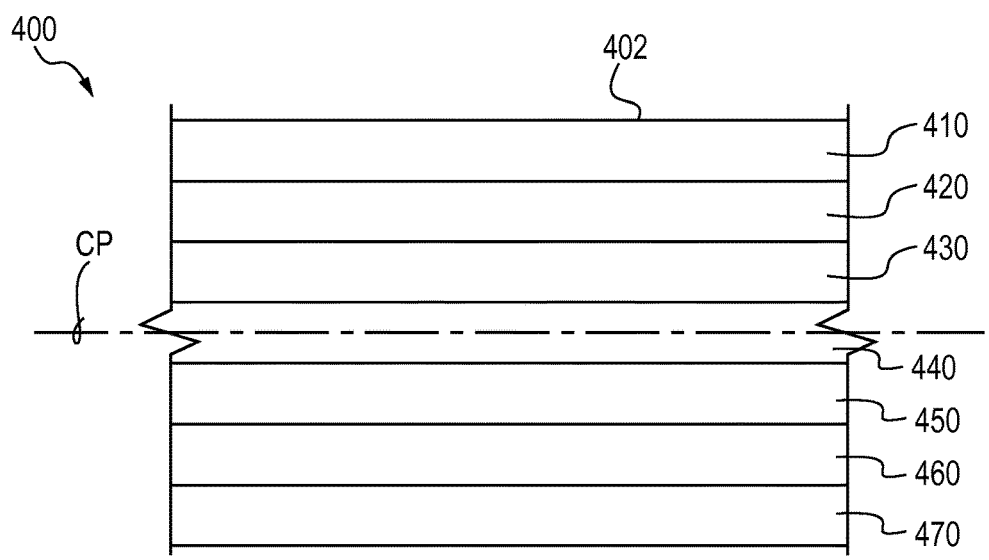
FIG. 4 is a schematic cross sectional view of another preferred embodiment multilayer polymeric film according to the present subject matter.

FIG. 4 depicts a seven layer laminate 400 similar to the previously described nine layer laminate 300 of FIG. 3. The laminate 400 comprises an outer layer 410 defining an outer face 402, a first moisture and odor barrier layer 420, a secondary moisture and odor barrier 430, an oxygen barrier 440 for reducing transmission of oxygen, a third moisture and odor barrier 450, a fourth moisture and odor barrier 460, and an inner layer 470. The moisture and odor barrier layers 420, 430, 450, and 460 generally correspond to the previously described moisture and odor barrier layers 330, 340, 360, and 370 of laminate 300 in FIG. 3. The outer layer 410 typically includes a polyolefin elastomer and particularly a propylene-ethylene copolymer such as the previously noted VERSIFY materials. In certain versions, the material is VERSIFY 2300. The oxygen barrier 440 is similar to the previously described oxygen barrier layer 350 of the laminate 300 of FIG. 3. The inner layer 470 can include a blend of an RF weldable polymer such as ethylene butyl acrylate (EBA) and a polyolefin elastomer such as the previously noted VERSIFY materials. In certain versions, the material is VERSIFY 2300. The oxygen barrier 440 is similar to the previously described oxygen barrier layer 350 of the laminate 300 of FIG. 3. The inner layer 470 can include a blend of an RF weldable polymer such as ethylene butyl acrylate (EBA) and a polyolefin elastomer such as the previously noted VERSIFY material. In certain versions of the laminate 400, one or both of the outer layer 410 and the inner layer 470 also includes an antiblock and slip masterbatch which is commercially available under the designation FSU-105E from A. Schulman. In certain versions, the laminate 400 of FIG. 4 may correspond to the construction of Table 12.

Another multilayer laminate embodiment of the present subject matter is presented below in Table 13.

TABLE 13

Preferred Embodiment Barrier Film

| Layer | Description | Thickness Typical | Thickness Preferred |
|---|---|---|---|
| A | Blend of Polyolefin Elastomer(s), Antiblock and Slip Masterbatch, and Optional Resin(s) | 12-18% | 15% |
| B | Polyolefin Elastomer(s) | 16-22% | 19% |
| C | Blend of COC(s) and Tie Agent | 6-14% | 10% |
| D | EVOH | 5-13% | 9% |
| E | Blend of COC(s) and Tie Agent | 6-14% | 10% |
| F | Polyolefin Elastomer(s) | 11-19% | 15% |
| G | Blend of RF Weldable Polymer(s) and Polyolefin Elastomer(s) and Tie Agent | 18-26% | 22% |

Referring to Table 13, layer A is an outermost layer and comprises a blend of one or more polyolefin elastomers and a masterbatch containing antiblock and slip agents. Layer A may also include one or more modifying resins. Optional coloring agents for example dyes, colorants, and/or pigments may be included in Layer A. Generally, the composition of Layer A includes from about 80% to about 85% of polyolefin elastomer(s) and optional resin(s), and from about 15% to about 20% of the noted masterbatch. The previously noted VERSIFY materials can be used for the polyolefin elastomer and the masterbatch. The resin may for example be low density polyethylene (LDPE). When one or more resins are included in conjunction with the polyolefin elastomer(s), a typical weight ratio of the resin to the polyolefin elastomer is 3:2, respectively, however, a wide range of weight ratios can be utilized such as for example from about 1:10, respectively, to about 10:1, respectively.

Layers B and F each include one or more polyolefin elastomers. Although a wide range of such materials can be used, a typical material is the previously noted VERSIFY 2300 available from Dow Chemical.

Layers C and E are each a blend of COC(s) or agents containing norbornene and one or more tie agents. It will be noted that each of layers C and E are located relatively close, i.e. immediately adjacent to, the center of the laminate. Generally, each layer includes a majority proportion of COC(s) and a minority proportion of tie agent(s). A typical weight proportion of COC(s) in each layer is about 80%. And, a typical weight proportion of the agent(s) in each layer is about 20%. However, it will be appreciated that the present subject matter includes a wide variety of proportions and combinations of components. The COC(s) are typically those previously described herein, and are preferably a blend of amorphous COC(s) and semi-crystalline (or elastic) COC(s). An exemplary combination of COC(s) is a blend of about 95% of the previously noted grade 9506 and about 5% of the previously noted grade E-140. It will be noted that a wide array of weight proportions can be utilized, and that other grades of COC(s) and/or types of norbornene containing agents could conceivably be used.

Layer D of Table 13 is ethylene vinyl alcohol (EVOH) and is as previously described Layer E of Table 11.

Layer G includes a blend of one or more RF weldable polymer(s), one or more polyolefin elastomer(s), and antiblock and slip masterbatch. The components can all be as previously described such as ethylene butyl acrylate (EBA) for the RF weldable polymer, VERSIFY 2300 for the polyolefin elastomer, and FSU-105E for the masterbatch. Generally, the masterbatch constitutes about 20% of the layer G composition and the RF weldable polymer and the polyolefin elastomer constitute about 80%. A typical weight ratio of the RF weldable polymer to the polyolefin elastomer in the composition of layer G is about 7:3, respectively. However, a wide array of weight ratios can be used such as from about 1:10, respectively to about 10:1, respectively. The laminate of Table 13 exhibits reduced noise levels. Although not wishing to be bound to any particular theory, this is believed to be due in part to locating the layers containing COC's relatively close to the central plane and/or immediately adjacent to the central layer the of the laminate.

Figure 5:
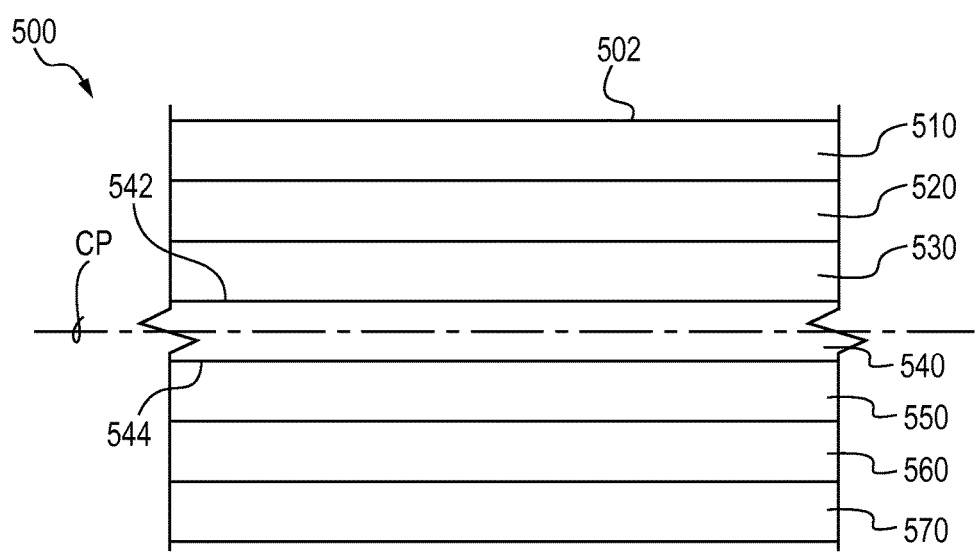
FIG. 5 is a schematic cross sectional view of another preferred embodiment multilayer polymeric film according to the present subject matter.

FIG. 5 illustrates a seven layer laminate 500 similar to the previously described seven layer laminate 400 of FIG. 4. The laminate 500 comprises an outer layer 510 defining an outer face, a first toughening or support layer 520, a first moisture and odor barrier layer 530, an oxygen barrier 540 for reducing transmission of oxygen, a second moisture and odor barrier layer 550, a second toughening or support layer 560, and an inner layer 570. The layer 540 is centrally located within the laminate 500 as a central plane CP of the laminate 500 extends through the layer 540, which in the particular embodiment under discussion, is also an oxygen barrier layer, defines a first face 542 and an oppositely directed second face 544. The COC-containing layer 530 is disposed immediately adjacent to the first face 542 of the central layer. And, the COC-containing layer 550 is disposed immediately adjacent to the second face 544 of the central layer. This arrangement promotes a low noise characteristic for the laminate 500. The moisture and odor barrier layers 530 and 550 generally correspond to the previously described moisture and odor barrier layers 330, 340, 360, and 370 of laminate 300 in FIG. 3; and layers 430 and 450 of laminate 400 in FIG. 4. The outer layer 510 generally corresponds to the previously described outer layer 410 of laminate 400 in FIG. 4. The toughening or support layers 520 and 560 generally correspond to the layer 320 of laminate 300 in FIG. 3. The oxygen barrier layer 540 generally corresponds to layer 350 in laminate 300 of FIG. 3 and layer 440 in laminate 400 of FIG. 4. The inner layer 570 generally corresponds to the layer 470 of laminate 400 in FIG. 4. In certain versions of the present subject matter, the laminate 500 may correspond to the construction of Table 13.

The present subject matter also provides various methods. In one aspect, the subject matter provides a method for forming a polymeric barrier film with excellent barrier properties. The method generally includes providing a polymeric barrier composition. Examples of such compositions include those previously described herein. The method also includes forming a film from the polymeric barrier composition. Extrusion techniques are preferred, however other known methods can be used for forming films. As explained herein, in certain embodiments, it is preferred that the at least one polymeric barrier composition includes a semi-crystalline cyclic olefin copolymer. In other embodiments, it is preferred that the at least one polymeric barrier composition includes ethylene vinyl alcohol (EVOH). In many of the embodiments, it is preferred that the polymeric barrier composition is free of halogens.

In one method according to the present subject matter, a method for reducing transmission of odorous species is provided. The method involves providing a multilayer film having a plurality of layers each including at least one COC, in which at least one of the layers includes a blend of a semi-crystalline COC and an amorphous COC. The method also involves positioning the film between a source of odorous species and a user.

In another aspect of the present subject matter, a method for reducing noise produced from flexure of a multilayer laminate having a plurality of COC-containing layers is provided. The method comprises arranging the plurality of layers such that the concentration of norbornene in each of the plurality of layers increases toward a central plane of the laminate as previously described herein. In still other aspects of techniques for reducing noise, domains of immiscible elastomeric polymer are formed in at least one of the layers of the plurality of layers as previously described. Additionally, in these methods, one or more layers of the plurality of layers includes a blend of a semi-crystalline COC and an amorphous COC.

The various layers and films can be extruded, coated, or otherwise formed by techniques known in the art. Co-extrusion techniques can also be utilized. For certain applications in which increased toughness and/or durability are desired, films can be blown.

The subject matter further provides methods of using the various compositions, films, and multilayer assemblies described herein. For example, a method for reducing transmission of odorous species is provided. The term "odorous species" as used herein refers to molecules or chemical species which are generally perceived by a user as unpleasant. A non-limiting example of odorous species is skatole or 3-methylindole. Another non-limiting example of an odorous species is hydrogen sulfide. The method comprises providing a semi-crystalline cyclic olefin copolymer, preferably as described herein. The method also comprises forming a film which includes the semi-crystalline cyclic olefin copolymer. And, the method also comprises positioning or placing the film between a source of the odorous species and a user. This latter operation typically involves forming the film into a container or pouch, or incorporating the film into such, and then using the container or pouch to hold, store, or collect material containing the odorous species.

The preferred embodiment barrier film constructions are believed to exhibit several advantages over currently known ostomy films. The preferred films are halogen-free and avoid the use of polyvinylidene chloride (PVDC). The preferred films are relatively quiet and exhibit significantly less "rustle". And, the preferred films exhibit superior odor blocking characteristics. Furthermore, the preferred films exhibit a combination of some and preferably all of these features. The film construction may be transparent or contain coloring agents.

The present subject matter also provides a wide array of articles using the barrier film(s) described herein. A non-limiting example of an article using the barriers described herein is an ostomy pouch. The barrier film(s) and preferably the multilayer barrier film(s) described herein can be joined with one or more other components. For example, in forming an ostomy pouch, a flexible wall container or pouch is formed from the multilayer films of Tables 7-9 and 11-13. Sealed regions are formed by thermal welding contacting face regions of the film so as to form a pouch with an enclosed interior. One or more outer external protective layers may be applied along the outer face such as face 2 of the assembly depicted in FIG. 1. The external layer(s) can be fabric, nonwoven, or other materials.

Figure 2:
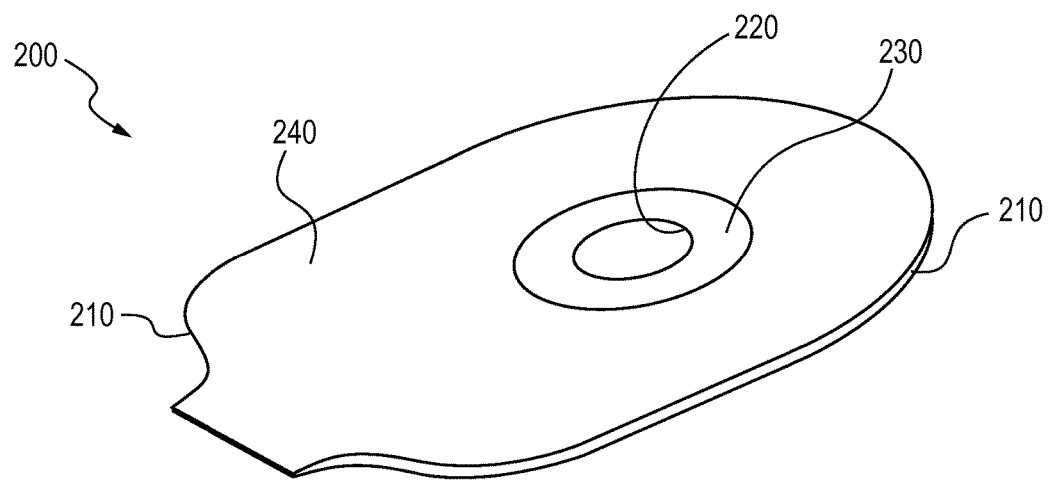
FIG. 2 is a schematic perspective view of a preferred embodiment ostomy bag or pouch according to the present subject matter.

FIG. 2 illustrates a preferred embodiment ostomy bag or pouch 200 in accordance with the present subject matter. The ostomy bag 200 includes one or more walls 240 sealed along an outer periphery or edge 210 to define a sealed interior accessible through an aperture 220. A sealing ring or wafer 230 is preferably used to seal the interface between the aperture 220 and a stoma. The wall 240 is preferably formed from the multilayer barrier assembly 100.

Multilayered barrier assemblies 100, 300, 400, and 500 as described herein are particularly useful in ostomy pouch applications, where security from odor, integrity of the device, and integrity of the underlying materials are requirements. Multilayered barrier films 100, 300, 400, and 500 can be die cut and heat sealed with conventional equipment, and are compatible with current attachment systems and ostomy pouch manufacturing practices. Since the multilayered barrier films 100, 300, 400, and 500 are moisture resistant both inside and out, the resulting ostomy pouch is capable of being worn during physical activity and showering. Optionally, with incorporation of a polymeric tempering additive, such as EVA copolymer, EAA copolymer, polybutylene, polybutylene copolymers, or combinations thereof, into various layers of the barrier films 100, 300, 400, and 500, the resulting ostomy pouch can be quieter when wrinkled or rustled during the movements of a wearer of such a pouch. In addition, other useful articles such as tapes, tubings, containers, transdermal drug-delivery patches and various packaging materials can also be formed from the multilayered barrier film 100, 300, 400, and 500. Thus, the multilayered barrier film 100, 300, 400, and 500 is useful to form or cover a protective environment from an external environment, such that moisture and/or gases cannot substantially pass through to a degradable product contained therein, or a surface covered thereby. For example, the multilayered barrier film 100, 300, 400, and 500 can be used to contain a food product or a pharmaceutical product in a protected environment, into which moisture and/or gases from the external environment cannot substantially pass. Similarly, the multilayered barrier film 100, 300, 400, and 500 can comprise a transdermal drug delivery patch, or medical tape, or an ostomy pouch, which protects the body of a mammal, or the waste products generated by the mammal, from degradation due to exposure to moisture and/or gases in the external environment.

Articles formed from the multilayered barrier structures need not be limited to nine or seven layered structures. In addition, these multilayered barrier structures can be further modified for specialty applications by adding additional layers thereto. For example, a specialty ostomy pouch comprising a multilayered barrier structure could be formed by laminating a fabric backing of a woven or nonwoven material (not shown) to a surface of the ostomy pouch. This fabric backing would serve to provide a soft layer against a wearer's skin, and thus make the ostomy pouch more comfortable and non-clinging.

A fabric backing could be applied to the multilayered barrier structure in a number of different ways. For example, a layer of a nonwoven material, formed from a polymer such as polypropylene, could be affixed to the multilayered barrier structure 100 by an intervening adhesive layer.

As an alternative, a fabric backing could be applied to the multilayered barrier structure 100, 300, 400, and 500 by affixing a web of melt blown microfibers thereto. For example, melt blown polymer microfibers could be hot melt extruded from a die into a high velocity air stream, and onto a surface of the multilayered barrier structure.

Many other benefits will no doubt become apparent from future application and development of this technology.

All patents, applications, standards, and articles noted herein are hereby incorporated by reference in their entirety.

It will be understood that any one or more feature or component of one embodiment described herein can be combined with one or more other features or components of another embodiment. Thus, the present subject matter includes any and all combinations of components or features of the embodiments described herein.

As described hereinabove, the present subject matter overcomes many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A multilayer barrier film comprising:
    at least one layer including a blend of cyclic olefin copolymers (COC), wherein the blend includes a semi-crystalline COC and a norbornene COC, wherein a total norbornene concentration of the norbornene COC in the at least one layer is from about 12% to about 60% by mole based upon the total moles of COCs in the layer; and
    a secondary barrier layer including ethylene vinyl alcohol (EVOH);
    wherein the semi-crystalline cyclic olefin copolymer has a glass transition temperature of from about −20° C. to about 20° C.

2. The multilayer barrier film of claim 1, wherein the total norbornene concentration of the norbornene COC in the at least one layer is from about 15% to about 55% based upon the total moles of COCs in the layer.

3. The multilayer barrier film of claim 1, wherein the at least one layer includes (i) a first layer including a semi-crystalline cyclic olefin copolymer (COC), and (ii) a second layer including a semi-crystalline cyclic olefin copolymer.

4. The multilayer barrier film of claim 3, wherein the semi-crystalline cyclic olefin copolymer in the first layer is the same as the semi-crystalline cyclic olefin copolymer in the second layer.

5. The multilayer barrier film of claim 1, wherein the ethylene vinyl alcohol has an ethylene content of from about 25% to about 50% by mole.

6. The multilayer barrier film of claim 5, wherein the ethylene vinyl alcohol has an ethylene content of from about 32% to about 48% by mole.

7. The multilayer barrier film of claim 6, wherein the ethylene vinyl alcohol has an ethylene content of from about 34% to about 48% by mole.

8. The multilayer barrier film of claim 1, wherein the at least one layer including the semi-crystalline cyclic olefin copolymer also includes at least one amorphous cyclic olefin copolymer.

9. A multilayer barrier film comprising:
at least one layer including a blend of cyclic olefin copolymers (COC), wherein the blend inclues a semi-crystalline COC and a norbornene COC, wherein a total norbornene concentration of the norbornene COC in the at least one layer is from about 12% to about 60% by mole based upon the total moles of COCs in the layer; and
a secondary barrier layer including ethylene vinyl alcohol (EVOH); and
at least one flexible support layer including one or more polymers selected from the group consisting of styrenic elastomers, polyolefins, and polyolefin elastomers and combinations thereof;
wherein the one or more polymers has a density of from about 0.75 to about 1.10 g/cm³.

10. The multilayer barrier film of claim 9, wherein the one or more polymers has a density of from about 0.85 to about 1.01 g/cm³.

11. The multilayer barrier film of claim 10, wherein the density is from about 0.860 to about 0.95 g/cm³.

12. The multilayer barrier film of claim 9, wherein the one or more polymers has a melt flow index of from about 0.1 to about 1,000 g/10 min.

13. The multilayer barrier film of claim 12, wherein the one or more polymers has a melt flow index from about 0.5 to about 100 g/10 min.

14. The multilayer barrier film of claim 1, further comprising:
an inner antimicrobial layer including at least one antimicrobial agent.

15. An article comprising the multilayer barrier film of claim 1.

16. The article of claim 15, wherein the article is an ostomy pouch.

17. A multilayer barrier film comprising:
at least one layer including semi-crystalline cyclic olefin copolymer (COC) having a melting temperature (Tm) of from about 70° C. to about 120° C., a glass transition temperature (Tg) of from about −20° C. to about 20° C. and a norbornene COC, wherein a norbornene content of the norbornene COC in the at least one layer is from about 12% to about 60% by mole based upon the total moles of COCs in the layer.

18. The multilayer barrier film of claim 17, wherein the at least one layer includes (i) a first layer including a semi-crystalline cyclic olefin copolymer (COC), and (ii) a second layer including a semi-crystalline cyclic olefin copolymer.

19. The multilayer barrier film of claim 18, wherein the semi-crystalline cyclic olefin copolymer in the first layer is the same as the semi-crystalline cyclic olefin copolymer in the second layer.

20. The multilayer barrier film of claim 17, further comprising:
a secondary barrier layer including ethylene vinyl alcohol (EVOH).

21. The multilayer barrier film of claim 17, wherein the ethylene vinyl alcohol has an ethylene content of from about 25% to about 50% by mole.

22. The multilayer barrier film of claim 17, wherein the ethylene vinyl alcohol has an ethylene content of from about 32% to about 48% by mole.

23. The multilayer barrier film of claim 17, wherein the ethylene vinyl alcohol has an ethylene content of from about 34% to about 48% by mole.

24. The multilayer barrier film of claim 17, wherein the at least one layer including the semi-crystalline cyclic olefin copolymer also includes at least one amorphous cyclic olefin copolymer.

25. The multilayer barrier film of claim 17, further comprising:
at least one flexible support layer including one or more polymers selected from the group consisting of styrenic elastomers, polyolefins, and polyolefin elastomers and combinations thereof.

26. The multilayer barrier film of claim 25, wherein the one or more polymers has a density of from about 0.75 to about 1.10 g/cm³.

27. The multilayer barrier film of claim 26, wherein the one or more polymers has a density of from about 0.85 to about 1.01 g/cm³.

28. The multilayer barrier film of claim 27, wherein the density is from about 0.860 to about 0.95 g/cm³.

29. The multilayer barrier film of claim 25, wherein the one or more polymers has a melt flow index of from about 0.1 to about 1,000 g/10 min.

30. The multilayer barrier film of claim 29, wherein the one or more polymers has a melt flow index of from about 0.5 to about 100 g/10 min.

31. The multilayer barrier film of claim 17, further comprising an inner antimicrobial layer including at least one antimicrobial agent.

32. An article comprising the multilayer barrier film of claim 17.

33. The article of claim 32, wherein the article is an ostomy pouch.

34. A method for reducing transmission of odorous species, the method comprising:
providing at least one layer including a blend of cyclic olefin copolymers (COC), wherein the blend includes a semi-crystalline COC and a norbornene COC, wherein a total norbornene concentration of the norbornene COC in the at least one layer is from about 12% to about 60% by mole based upon the total moles of COCs in the layer;
forming a barrier film including the at least one layer including a blend of cyclic olefin copolymers (COC); and
positioning the barrier film between a source of odorous species and a user;
wherein the semi-crystalline cyclic olefin copolymer has a glass transition temperature of from about −20° C. to about 20° C.

35. The method of claim 34, wherein the total norbornene concentration in the layer is from about 15% to about 55% by mole.

36. The method of claim 34, wherein the odorous species is selected from the group consisting of skatole and hydrogen sulfide.

37. The multilayer barrier film of claim 1, further comprising:
at least one support layer including a polyolefin elastomer.

38. The multilayer barrier film of claim 37, wherein the at least one support layer is disposed at a distance from the central plane greater than the maximum distance between any one of the plurality of layers and the central plane.

39. The multilayer barrier film of claim 1, wherein the outermost layers of the plurality of layers include a majority proportion of at least one semi-crystalline COC and a minority proportion of at least one amorphous COC.

40. The multilayer barrier film of claim 1, wherein the innermost layers of the plurality of layers include a majority proportion of at least one amorphous COC and a minority proportion of at least one semi-crystalline COC.

41. A multilayer barrier film defining a central layer through which extends a central plane, the central layer defining a first face and an oppositely directed second face, the barrier film comprising:
a first layer including at least one semi-crystalline COC having a glass transition temperature of −20° C. to 20° C., the first layer disposed immediately adjacent to the first face of the central layer;
a second layer including at least one semi-crystalline COC, the second layer disposed immediately adjacent to the second face of the central layer.

42. The multilayer barrier film of claim 41, wherein the central layer is a barrier layer for reducing transmission of oxygen.

43. The multilayer barrier film of claim 41, further comprising:
at least one support layer including a polyolefin elastomer.

44. The multilayer barrier film of claim 43, wherein the at least one support layer is disposed at a distance from the central plane greater than the maximum distance between any one of the first layer and the second layer and the central plane.

45. The multilayer barrier film of claim 41, further comprising:
at least one of an outer layer and an inner layer at least one of which includes an RF weldable polymer.

46. The multilayer barrier film of claim 41, wherein each of the first layer and the second layer includes a majority proportion of at least one amorphous COC and a minority proportion of at least one semi-crystalline COC.

47. An article comprising the barrier film of claim 41.

48. The article of claim 47, wherein the article is an ostomy pouch.

49. The method for reducing transmission of odorous species of claim 34, the method further comprising:
providing a multilayer film having a plurality of layers each including at least one COC, at least one of the layers including a blend of a semi-crystalline COC and an amorphous COC.

50. The method of claim 49, wherein the outermost layers of the plurality of layers include a majority proportion of at least one semi-crystalline COC and a minority proportion of at least one amorphous COC.

51. The method of claim 49, wherein the innermost layers of the plurality of layers include a majority proportion of at least one amorphous COC and a minority proportion of at least one semi-crystalline COC.

* * * * *